(12) United States Patent
Sauer

(10) Patent No.: US 7,731,727 B2
(45) Date of Patent: Jun. 8, 2010

(54) MEDICAL INSTRUMENT TO PLACE A PURSESTRING SUTURE, OPEN A HOLE AND PASS A GUIDEWIRE

(75) Inventor: Jude S. Sauer, Rochester, NY (US)

(73) Assignee: LSI Solutions, Inc., Victor, NY (US)

( * ) Notice: Subject to any disclaimer, the term of this patent is extended or adjusted under 35 U.S.C. 154(b) by 748 days.

(21) Appl. No.: 11/411,626

(22) Filed: Apr. 26, 2006

(65) Prior Publication Data

US 2007/0255296 A1 Nov. 1, 2007

(51) Int. Cl.
*A61B 17/04* (2006.01)
(52) U.S. Cl. .................... 606/144; 606/139; 606/148
(58) Field of Classification Search ............... 606/139, 606/144, 148
See application file for complete search history.

(56) References Cited

U.S. PATENT DOCUMENTS

| | | | | |
|---|---|---|---|---|
| 5,080,663 A * | 1/1992 | Mills et al. | .................. | 606/144 |
| 5,336,229 A * | 8/1994 | Noda | .......................... | 606/144 |
| 5,431,666 A * | 7/1995 | Sauer et al. | .................. | 606/139 |
| 5,527,322 A * | 6/1996 | Klein et al. | .................. | 606/144 |
| 5,667,517 A * | 9/1997 | Hooven | ...................... | 606/151 |
| 5,700,273 A * | 12/1997 | Buelna et al. | ............... | 606/148 |
| 5,792,152 A * | 8/1998 | Klein et al. | .................. | 606/144 |
| 5,792,153 A * | 8/1998 | Swain et al. | ................. | 606/144 |
| 5,836,955 A * | 11/1998 | Buelna et al. | ............... | 606/148 |
| 5,947,983 A * | 9/1999 | Solar et al. | .................. | 606/144 |
| 6,024,747 A * | 2/2000 | Kontos | ........................ | 606/144 |
| 6,036,699 A * | 3/2000 | Andreas et al. | ............. | 606/139 |
| 6,206,893 B1 * | 3/2001 | Klein et al. | .................. | 606/144 |
| 6,368,334 B1 * | 4/2002 | Sauer | .......................... | 606/139 |
| 6,461,366 B1 * | 10/2002 | Seguin | ........................ | 606/144 |
| 6,517,553 B2 * | 2/2003 | Klein et al. | .................. | 606/144 |
| 6,533,796 B1 * | 3/2003 | Sauer et al. | .................. | 606/144 |
| 6,551,330 B1 | 4/2003 | Bain et al. | | |
| 7,060,079 B2 * | 6/2006 | Wulc et al. | .................. | 606/148 |
| 7,287,682 B1 * | 10/2007 | Ezzat et al. | ............... | 227/175.1 |
| 7,390,328 B2 * | 6/2008 | Modesitt | ...................... | 606/144 |
| 7,449,024 B2 * | 11/2008 | Stafford | ...................... | 606/144 |
| 2004/0138704 A1 * | 7/2004 | Gambale et al. | ............ | 606/213 |
| 2004/0158125 A1 * | 8/2004 | Aznoian et al. | ............. | 600/106 |

OTHER PUBLICATIONS

Albert Decker, M.D. and Thomas H. Cherry, M.D., *Culdoscopy*, American Journal of Surgery New Series vol. LXIV No. 1, Apr. 1944, pp. 40-44 New York, NY.

(Continued)

*Primary Examiner*—Darwin P Erezo
(74) *Attorney, Agent, or Firm*—Stephen B. Salai, Esq.; Brian B. Shaw, Esq.; Harter Secrest & Emery LLP

(57) ABSTRACT

A therapeutic instrument for the ergonomic, effective and safe opening and closing of targeted remote tissue sites; includes a pistol grip style handle with a hand activated lever for needle deployment and, optionally, with features to control tissue cutting and guide wire installation; also incorporates a specialized elongated rigid or flexible instrument shaft, which enables vacuum assisted holding of tissue at a uniquely contoured distal tip, where placement of a suture in a purse string configures occurs along with, if desired, tissue cutting and guide wire passage.

27 Claims, 26 Drawing Sheets

OTHER PUBLICATIONS

John R. Saltzman, M.D., *The Future of Endoscopic Technology*, Digestive Disease Week 2004, New Orleans, LA.

Marvin Ryou, M.D. et al, *Evaluating an Optimal Gastric Closure Method for Transgastric Surgery* (Abstract submitted for Presentation at SAGES, 2006).

Derek G. Fong, M.D., et al., *Transcolonic Access to the Peritoneal Cavity Using a Novel Incision and Closure Device*, (Abstract submitted for presentation at the Digestive Disease Week Conference, 2006.

\* cited by examiner

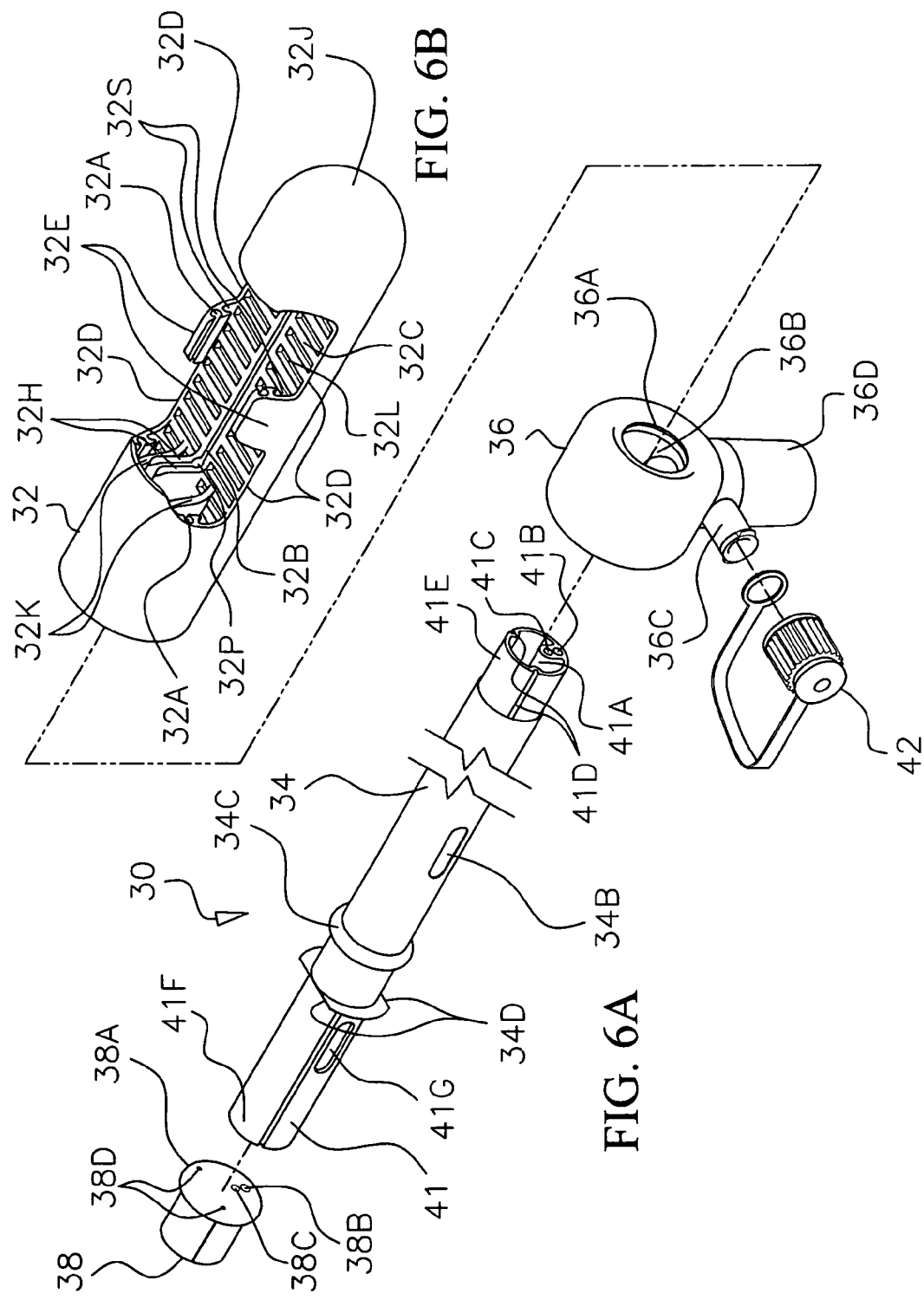

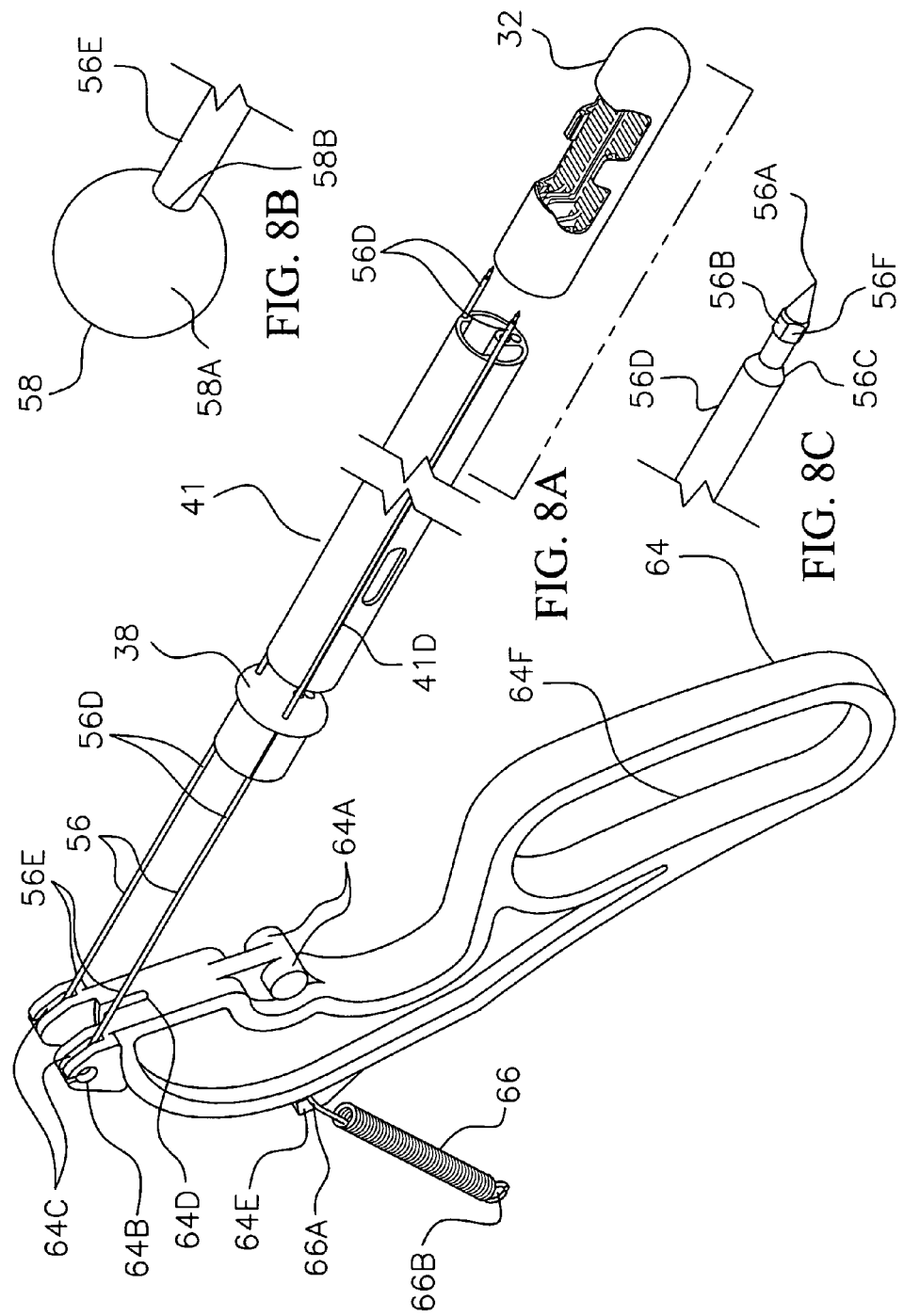

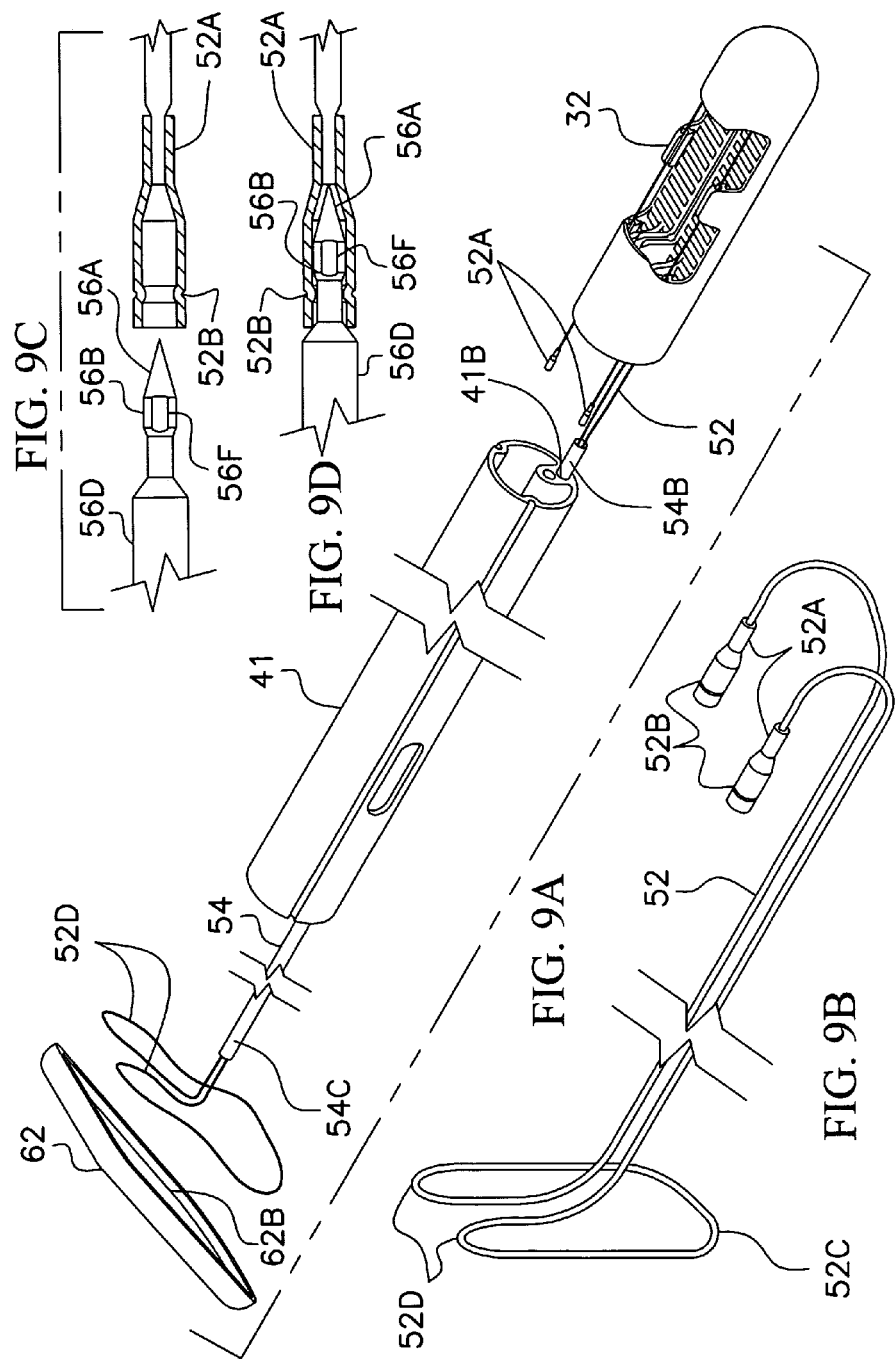

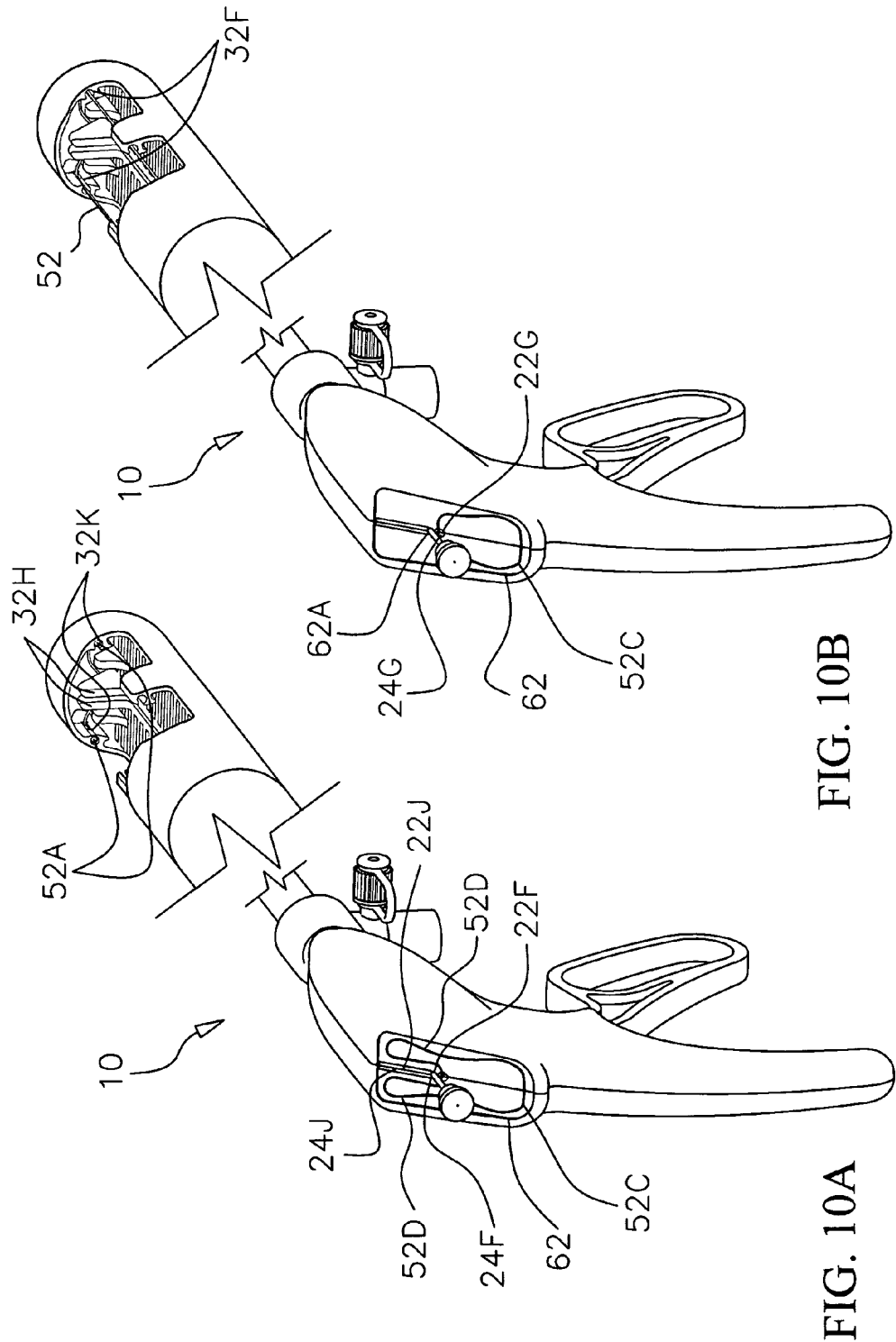

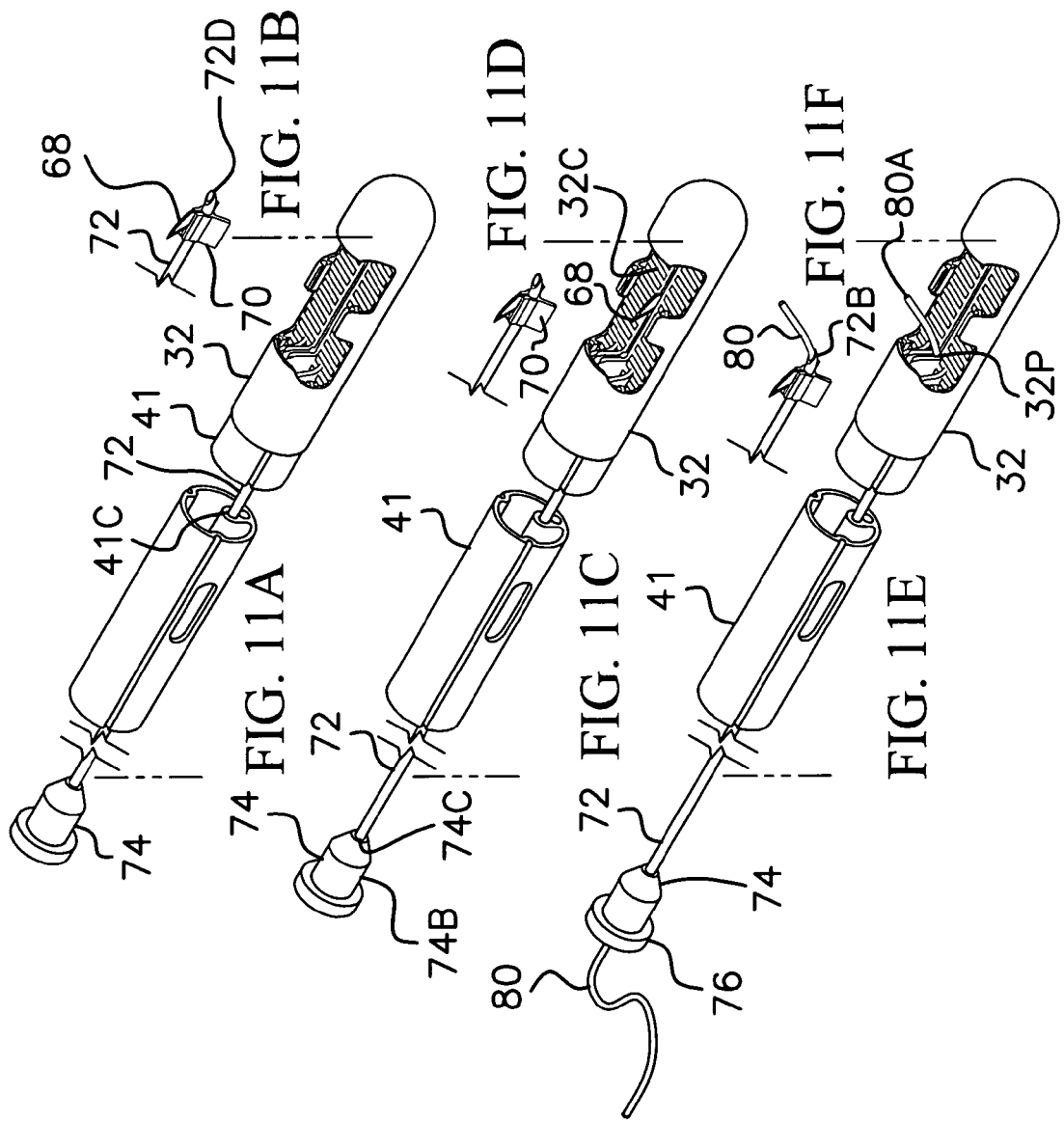

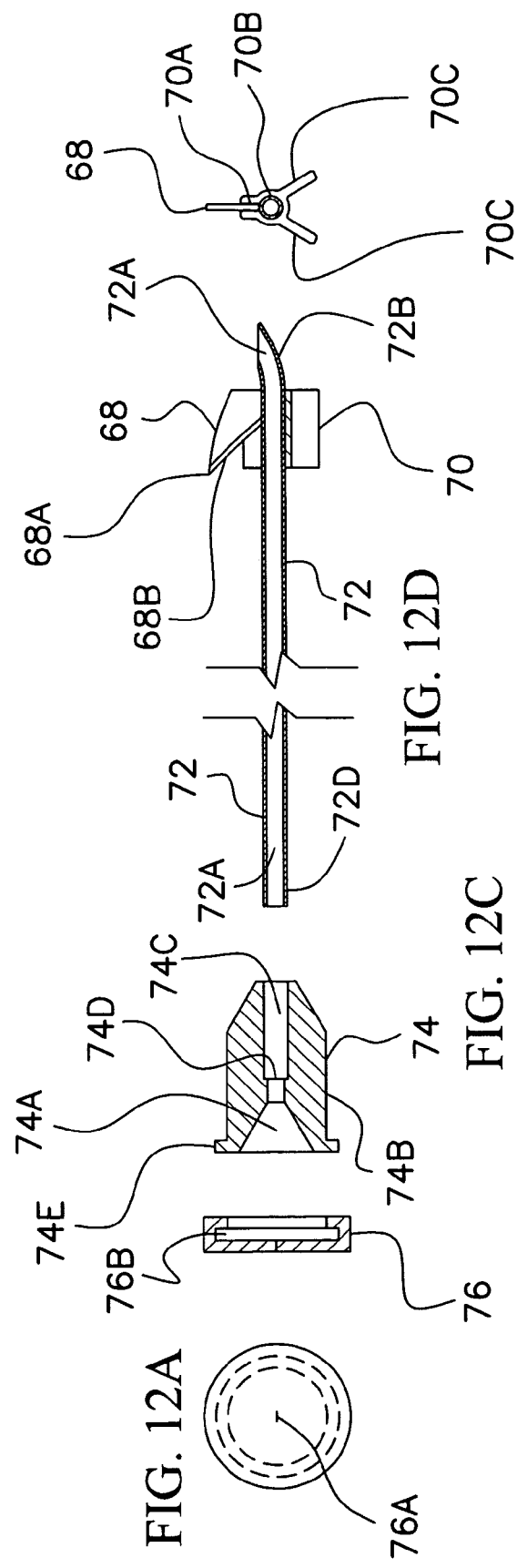

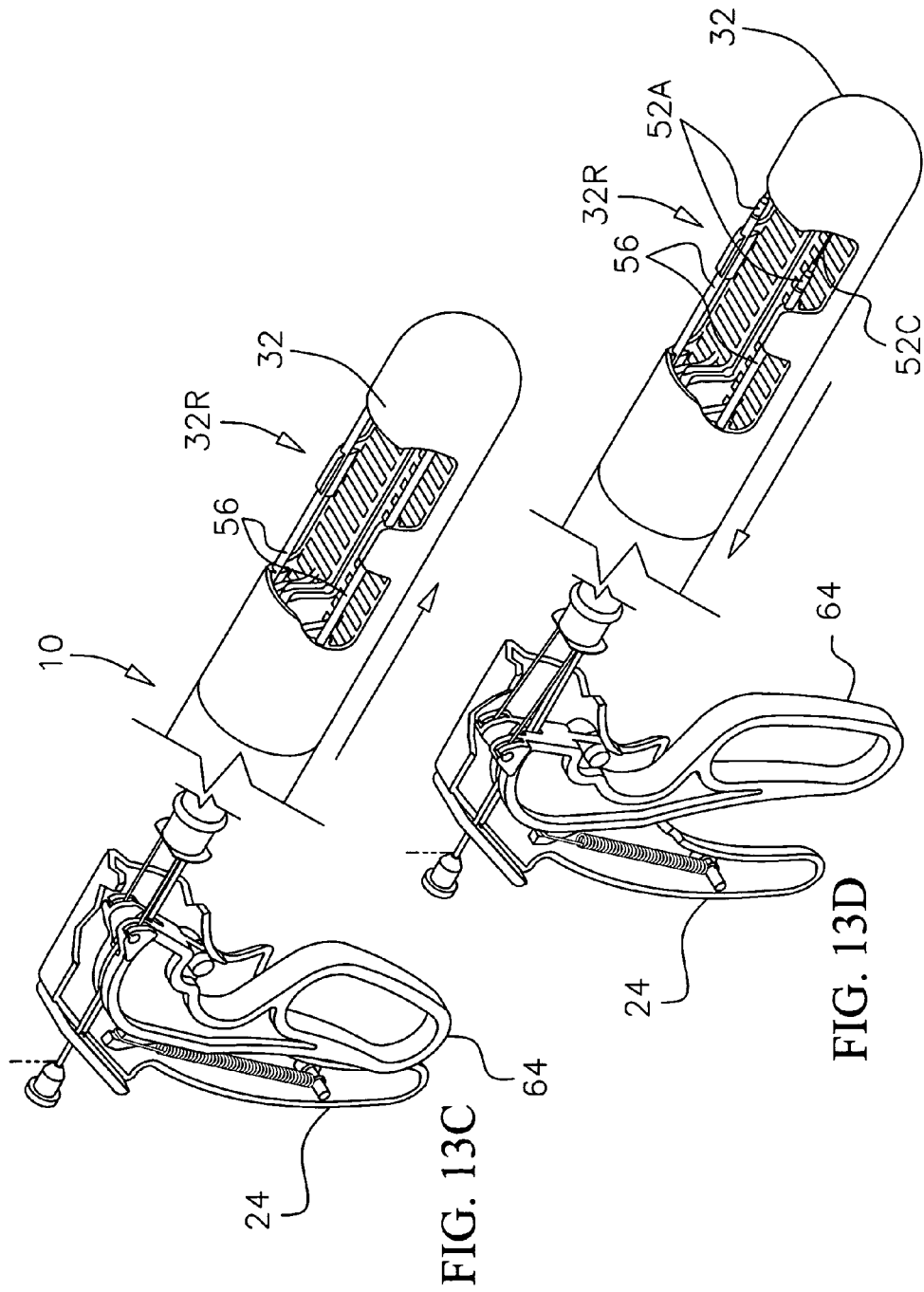

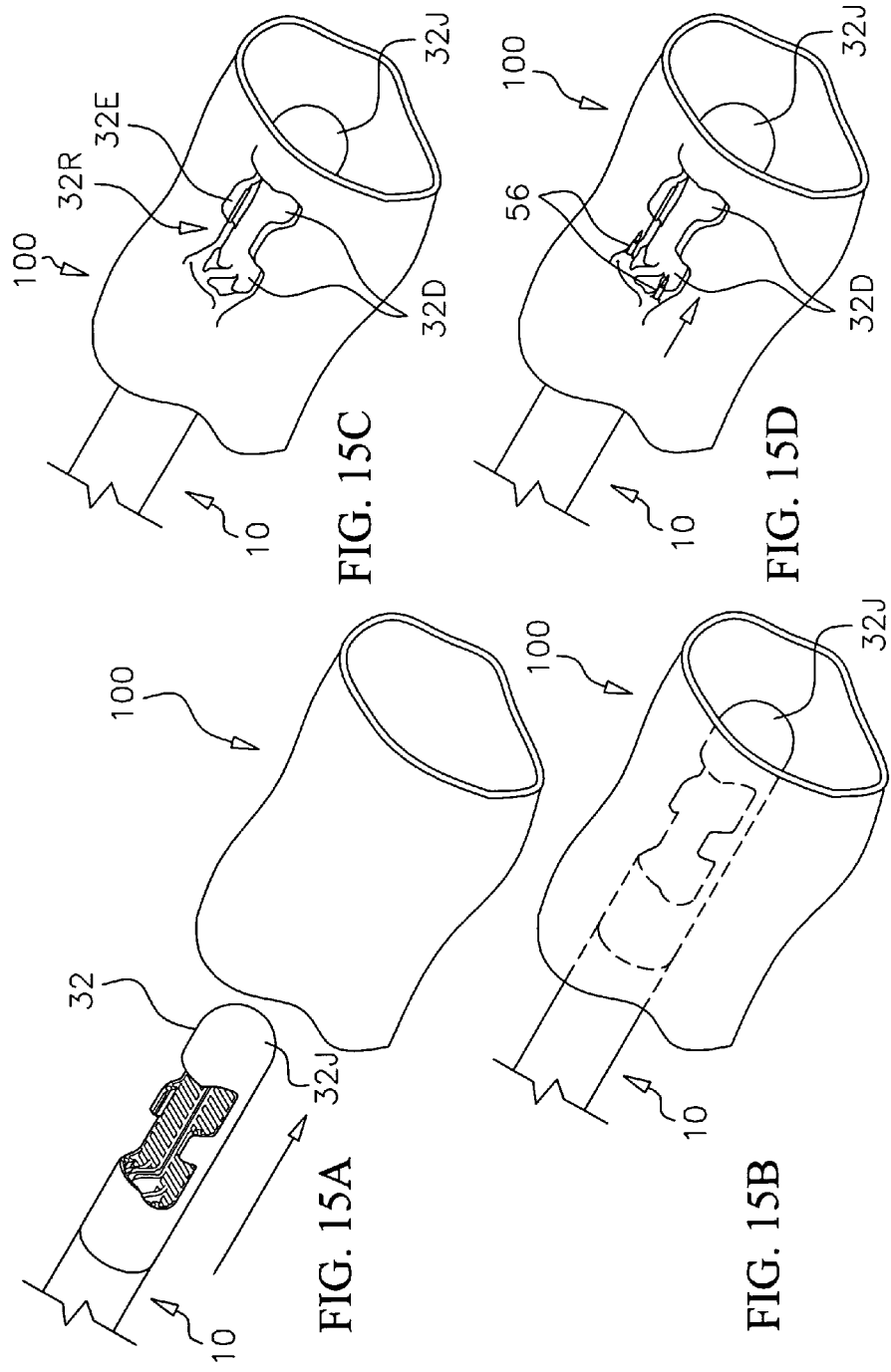

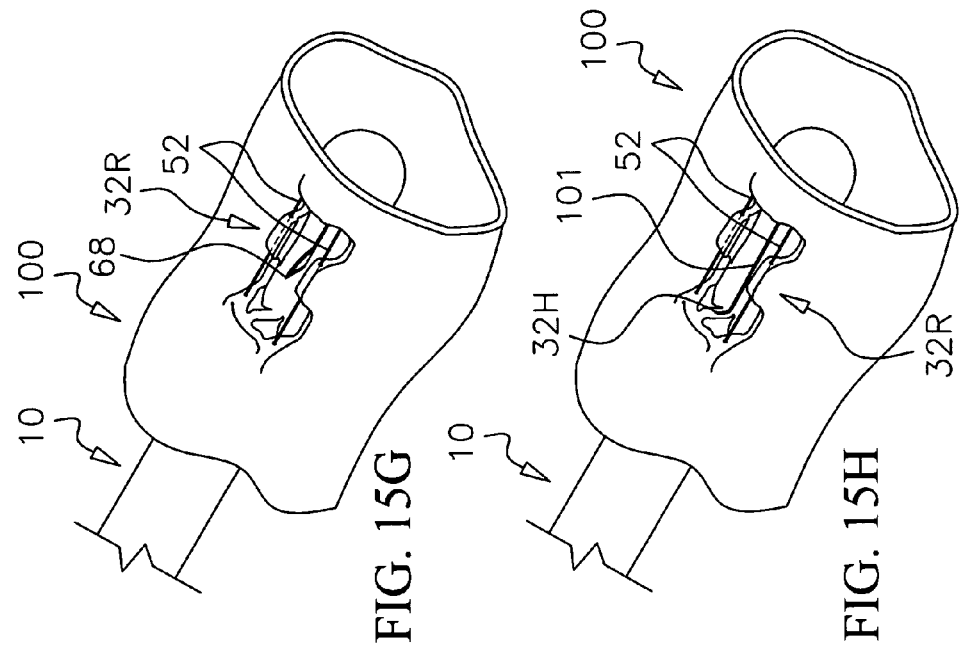
FIG. 15E
FIG. 15F
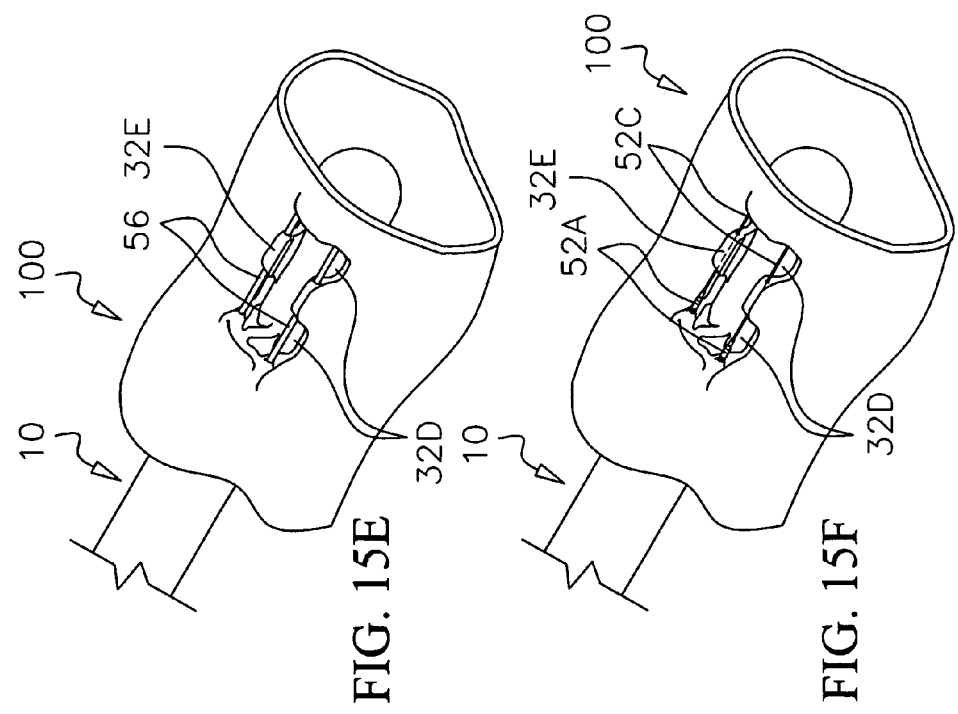
FIG. 15G
FIG. 15H

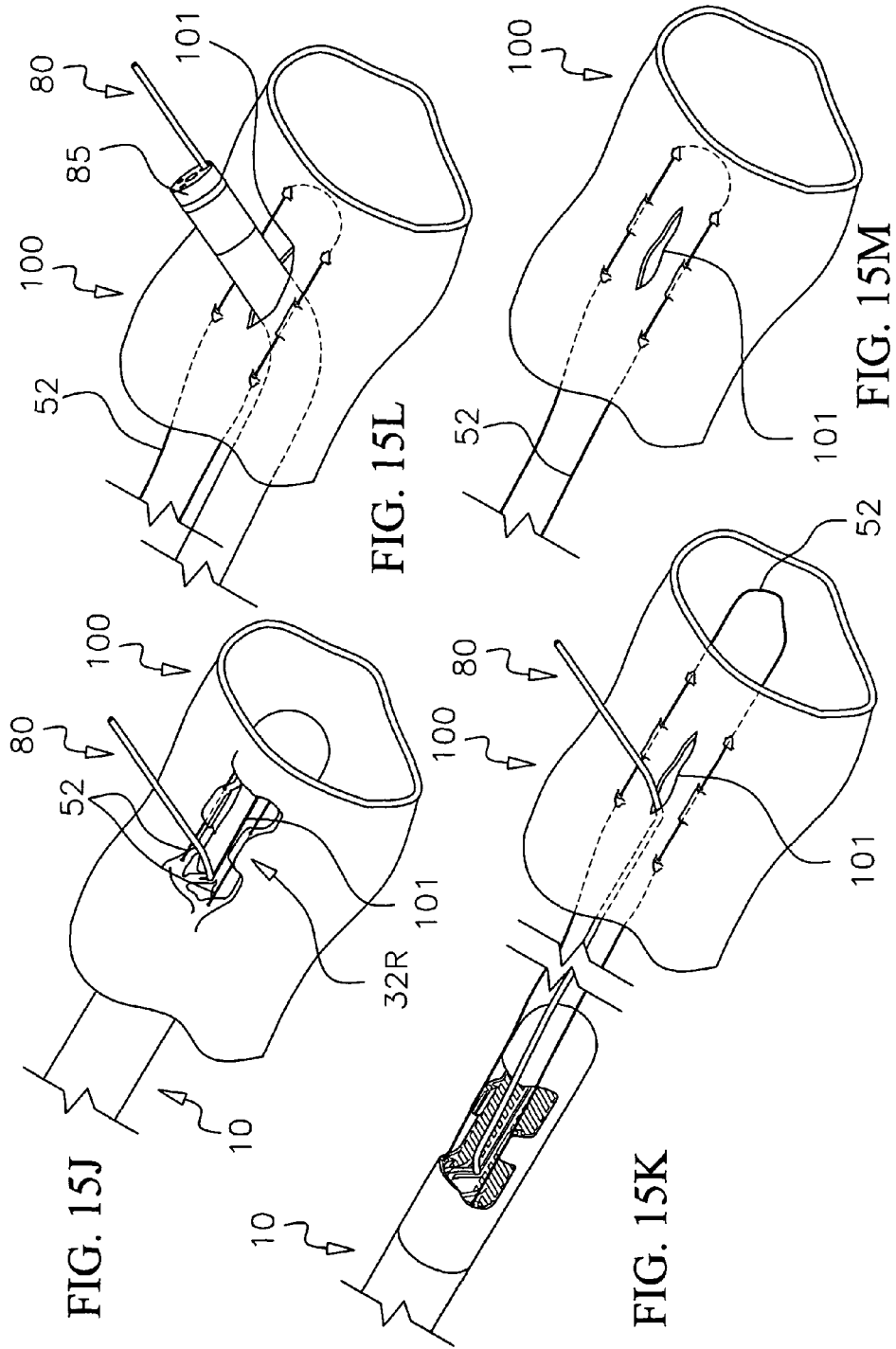

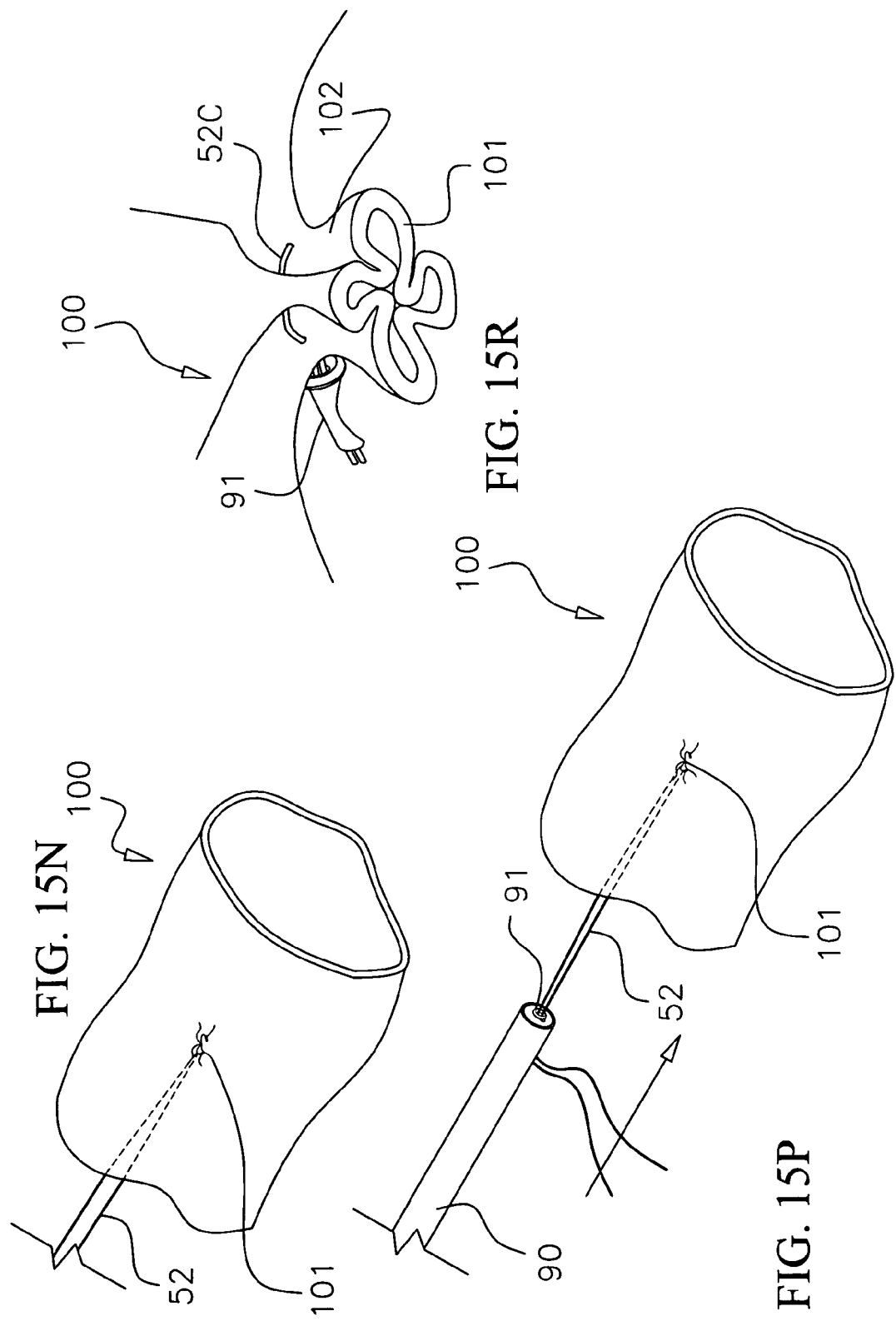

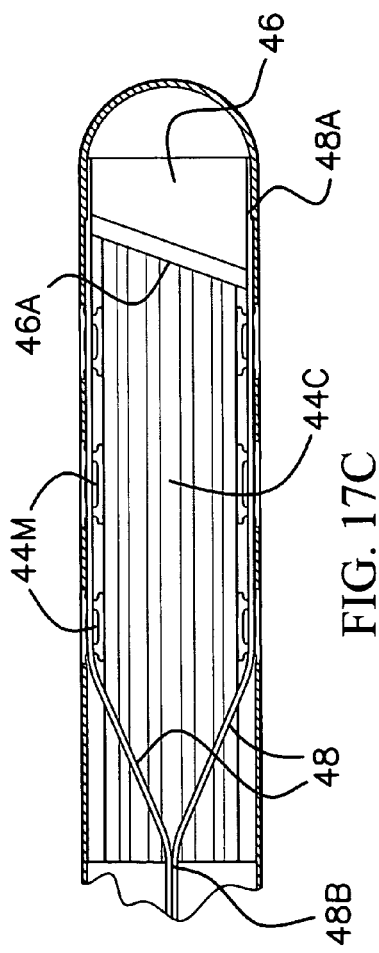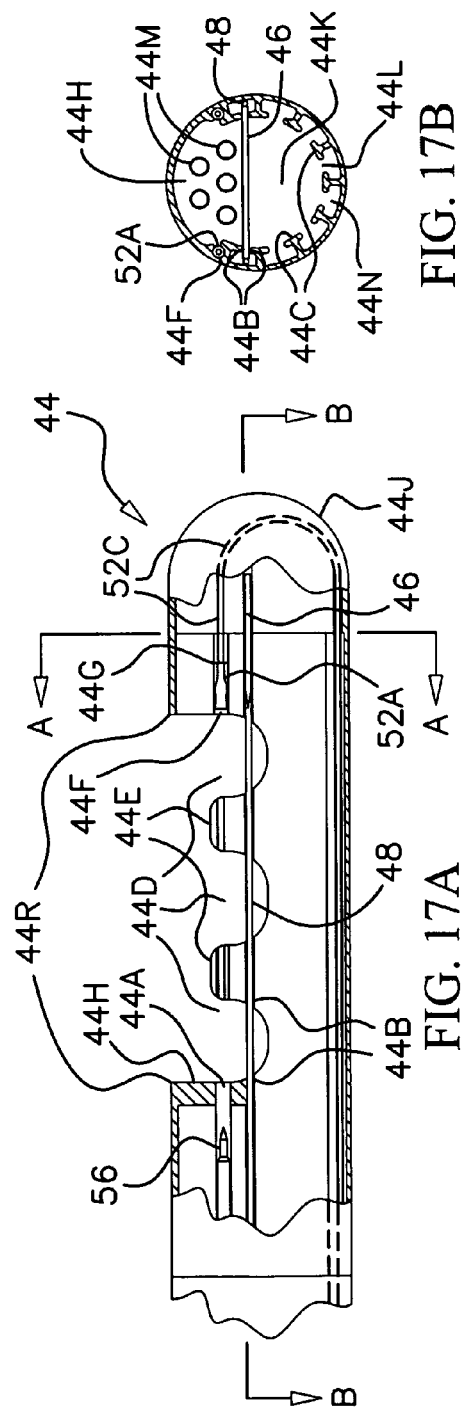
FIG. 17C
FIG. 17B
FIG. 17A

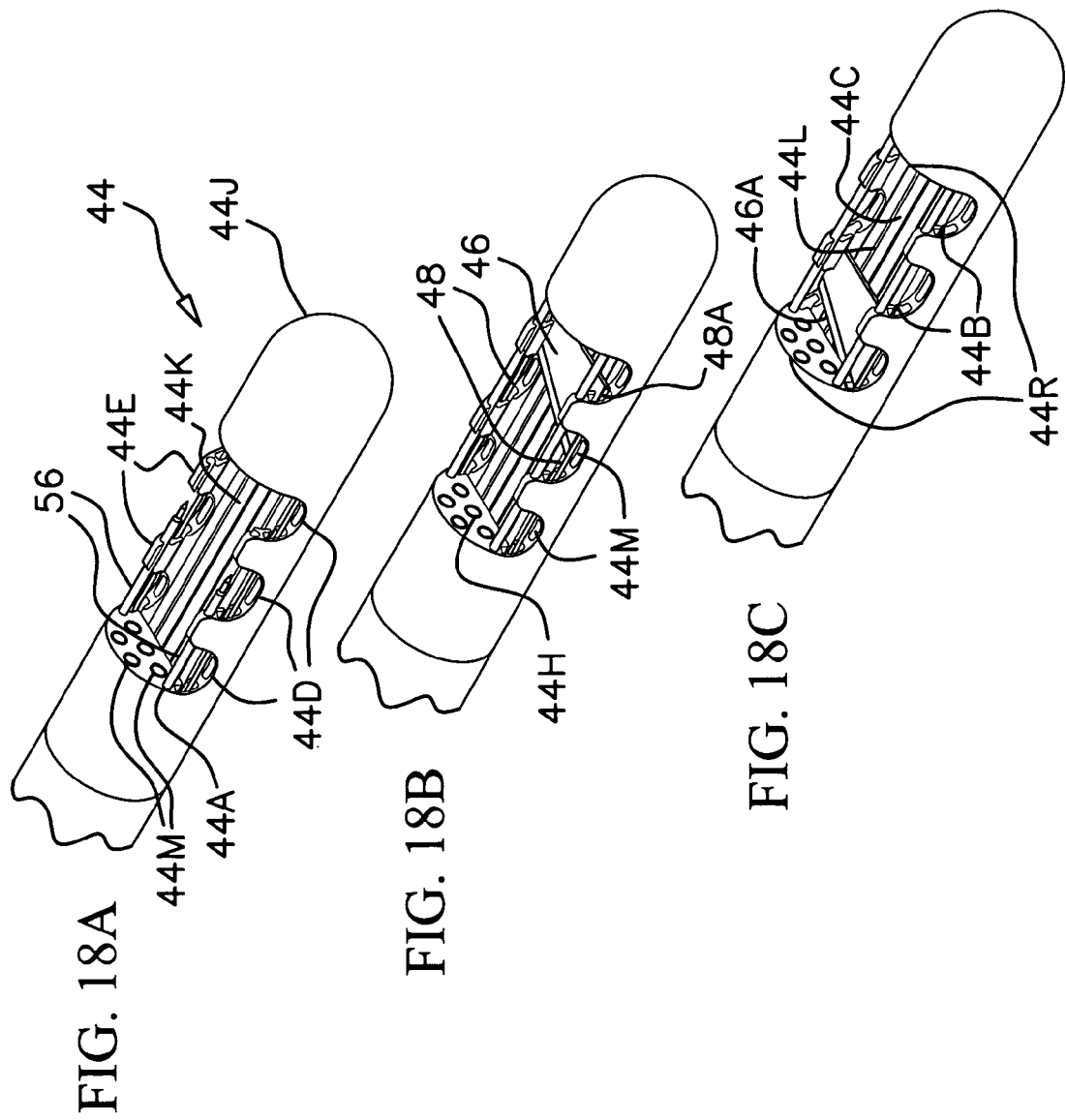

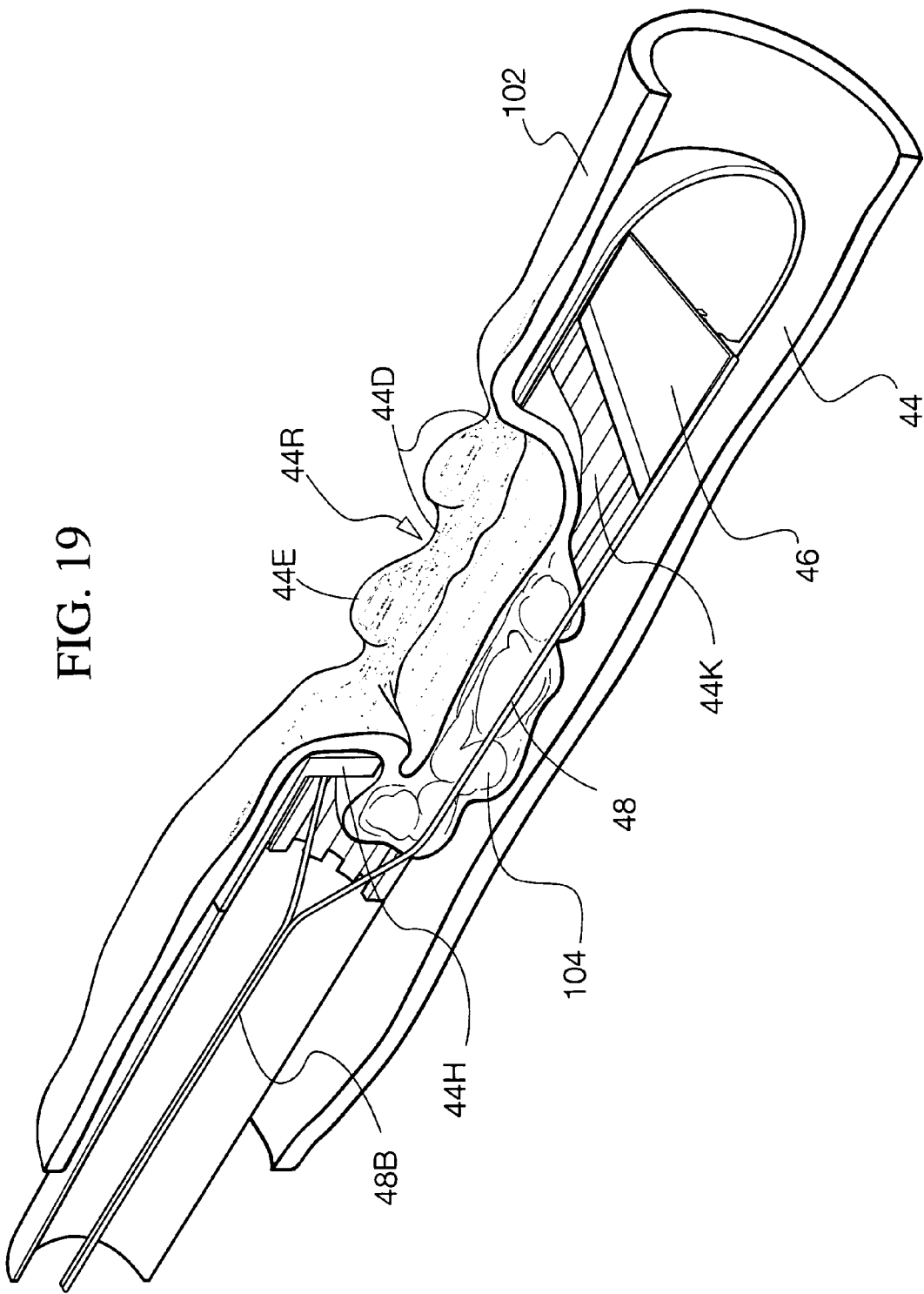

MEDICAL INSTRUMENT TO PLACE A PURSESTRING SUTURE, OPEN A HOLE AND PASS A GUIDEWIRE

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A "SEQUENCE LISTING"

Not applicable.

BACKGROUND OF THE INVENTION

1. Field of the Invention

This invention relates generally to a medical device for placement of a purse string suture in tissue and more particularly to such a device that can also cut tissue and enable placement of a guide wire through the cut opening. More particularly, this invention relates to a method and apparatus in which living tissue is positioned using vacuum within a contoured opening located near the end of the device, which also provides for the simultaneous passage of two needles through multiple points in the held tissue. After traversing the tissue, the needles engage and pick up both ends of a segment of suture and subsequently pull the suture ends back through the targeted tissue to facilitate a reliably customized suture placement. A slidable mechanism is provided to cut the held tissue and also, when desired, to enable the passage of a guide wire through the cut opening. This invention is particularly useful for the creation of closable openings in tissue structures or for safely harvesting deeper samples from the walls of tissue structures.

2. Description of Related Art

Despite all of the advances of modern medicine, many seemingly simple patient interventions still present significant challenges regarding their safe and reliable implementation. For many patients, substantial therapeutic advantage could be offered by a technology facilitating rapid and reliable cutting open and closing of a remote tissue sites.

Efforts to improve a physician's ability to do more than just see the outer characteristics of a patient are essential to modern health care. For centuries, health care practitioners have used existing external anatomic features for gaining limited access to a patient's internal structures for diagnostic or therapeutic interventions. Without the right equipment, health care providers can only use their direct vision to view their patient's body surfaces, exposed orifices or anatomy exposed through open incisions or wounds. The use of radiographic techniques (e.g., X-ray, CT and MRI), endoscopic techniques (e.g., colonoscopy, gastroscopy, cystoscopy, bronchoscopy) and open or laparoscopic surgery, along with combinations of these modalities, now routinely provide clinically significant data and the opportunity for direct therapeutic interventions.

An endoscopic technique for viewing internal patient body cavities was first reported in 1805. Important advancements in less invasive techniques (e.g., laparoscopic surgery in 1901, flexible fiber optic endoscopes in 1957, endoscopic retrograde cholangiopancreatography (E.R.C.P) in 1968, laparoscopic cholecystectomy in 1988, etc.) helped usher in this era of modern medicine. Improvements to endoscopic technology continue to yield significant improvements in therapeutics.

Many patients could benefit from a physician's ability to gain access to internal body locations through an organ structure naturally communicating with an existing external orifice instead of through a painful incision in the skin and its underlying muscle and fascial structures. Interventions using this alternative approach have come to be called "Natural Orifice Translumenal Endoscopic Surgery" or its acronym, "NOTES," procedures.

Examples of excellent potential access points to facilitate minimally invasive NOTES procedures include: safe entry to and exit from the peritoneal cavity through a wall of the stomach (i.e., transgastric), via the mouth, through the rectum and sigmoid colon (i.e., transcolonic), via the anus, or through the posterior fornix of the vagina (i.e., transvaginal) via the external vaginal opening. Generally, access to other body parts or compartments through the wall of a tissue structure is commonly referred to as "transmural" (i.e., through the wall) access; more specifically, gaining such access through the wall of a tubular tissue structure, from the inside (i.e., the lumen) to the outside, is commonly called an extralumenal (i.e., outside of the lumen) approach.

The proper utilization of naturally existing orifices to provide initial entry for therapeutic interventions may minimize many of the risks and morbidities of more traditional open laparotomy or laparoscopic surgery. To support a paradigm shift away from surgery requiring skin incisions, it would be helpful to have a technology, like the present invention, that could appropriately hold remote tissue, reliably provide a suture to subsequently secure it closed, safely cut it and to enable the placement of a temporary guide wire to facilitate easier instrument passage.

In the *American Journal of Surgery*, April 1944, Drs. Decker and Cherry published a manuscript describing a procedure they "termed culdoscopy." They reported use of the "vaginal route" to access the peritoneal cavity for viewing internal structures and for instrument manipulations. They presented the "Decker culdoscope" and a "trochar and cannula set" for "puncturing the posterior vaginal wall." Examples of the transmural procedures they reported include rupture of small cysts, biopsy of ovaries, testing the fallopian tubes for patency and tubal ligation for sterilization.

A recent resurgence of interest in the transmural NOTES procedures has lead to several new reports regarding the use of this approach in mostly animal experimental models. A gastroscopic "pancreatic necrosectomy" procedure was presented the internationally renowned "Digestive Disease Week" conference in 2003. This presentation reported the use of a gastroscopic instrumentation to exit through the stomach and debride a pancreas of necrotic tissue. At the "Digestive Disease Week" conference in 2004, investigators presented their "successful peroral transgastric ligation of fallopian tubes . . . in a survivor porcine model." Other investigators presented transgastric biliary surgery, including the removal of a gallbladder from a pig. While the use of an instrument called the Eagle Claw V (Olympus Medical Systems Corportion, Tokyo, Japan) was reported for transgastric suturing of intraperitoneal tissue structures like a splenic artery; it was not used to close the transmural access site. Other investigators suggested the use of computer-controlled robots to aid in transgastric surgery. A conclusion stated, "clearly, there is a need for better instrumentation."

Academic leaders in this area wrote an authoritative publication entitled, "ASGE/SAGES Working Group on Natural Orifice Translumenal Endoscopic Surgery—White Paper—

October 2005." They reviewed recent porcine research and noted a report of a human transgastric appendectomy. While the paper mostly highlighted the per oral transgastric approach, they also mentioned the promise of the transcolonic and transvaginal access. These expert laparoscopic surgeons and endoscopists "(A)ll agreed that Translumenal Endoscopic Surgery could offer significant benefits to patients such as less pain, faster recovery, and better cosmesis than current laparoscopic techniques." They stated, "(I)t seems feasible that major intraperitoneal surgery may one day be performed without skin incisions. The natural orifices may provide the entry point for surgical interventions in the peritoneal cavity, thereby avoiding abdominal wall incisions."

This Natural Orifice Translumenal Endoscopic Surgery— White Paper identified "ten critical areas that will impact the safety of NOTES." The first two areas listed by these authors are directly addressed by the present invention. From "Table 2. Potential Barriers to Clinical Practice," the first and second listed areas are, respectively, "Access to peritoneal Cavity" and Gastric (intestinal) closure." They state that while the "most important areas of initial study are . . . safe peritoneal access and secure gastric closure," the "optimal techniques to do so . . . are unknown."

The long term results of recent efforts to endoscopically suture the native lining of remote tissue sites to achieve tissue thickening and/or tightening (i.e., in medical terms, a "plication") have proved to be relatively disappointing. Clinical investigations exploring such suture-mediated changes to tissue have typically shown excellent short-term realization of the desired symptom relief. However, without any other wound closure site preparation, over time, the sutures alone tend to loose their ability to hold tissue together for thickening or tightening. Examples of encouraging short termed success, but later disappointment, are included in most of the published clinical study's of the use of the ESD™, Endoscopic Suturing Device (manufactured by LSI SOLUTIONS®, Victor, N.Y.) or the EndoCinch® (manufactured by Bard®, Bellarica, Mass.); the encouraging early relief from endoscopically placed suture alone (without site preparation) at the distal esophagus in patients with gastroesophageal reflux disease or at the dilated surgically created stomach to small bowel connections (i.e., gastrojejunal anastomoses) in gastric bypass patients usually faded completely within two years.

Thousands of patients suffering from gastroesophageal reflux disease (GERD) have undergone endoscopic suturing using commercially available products in conjunction with gastroscopy. Despite highly encouraging initial symptom relief, most patients progressively returned to their baseline state of "heart burn" or other discomfort over weeks or months following their procedure. Without proper healing, living tissue tends to return to its prevailing state. Sutures or surgical staples alone typically can only provide a temporary mechanical arrangement to promote tissue healing. In most cases, the body has to respond and take over the functional process. Almost all patients receiving suture thickening and tightening of their esophagus adjacent to the stomach only had a few stitches placed to bulk up and narrow the native lining (called the mucosa) of the esophagus against itself. Over time, the bodies of these patients overcame the presence of the foreign material (i.e., the suture) and the walls of their distal esophagus attenuated and loosened.

Laboratory research indicates that successful long-term plication to thicken and tighten the distal esophagus is more achievable by stimulating the tissue to actually heal into the desired configuration, instead of relying solely on sutures to hold the tissue in position. Research in our porcine laboratory indicated that methods using tissue cutting or burning to promote healing at distal esophageal wound closure sites were worthy of further study. A study, entitled, "Mucosal Apposition in Endoscopic Suturing," published by colleagues at the Cleveland Clinic, Cleveland, Ohio, reported promising results through the use of cauterizing the esophageal mucosa prior to suturing. Excellent clinical results were also reported in pediatric GERD patients who received cautery mediated wound site preparation to take away the protective mucosal lining of the esophagus and expose the inner healing tissues in preparation prior to ESD suturing.

For some bariatric patients with failed gastric bypass procedures, the endoscopic use of suturing to narrow the opening between the reduced stomach and its outflow into the by-passed small bowel has only produced acceptable, durable improvements in patients who have also received suturing site preparation to remove some mucosa and stimulate the underlying tissue to realize long term healing. Dr. Christopher Thompson's pioneering team in Boston report the largest series of patient amelioration by using suture to reduce the diameter of the connection between the functional stomach and small bowel. Their satisfactory results only came after improving their anastomotic tightening technique to also include suture site preparation.

To achieve long-term tissue thickening and tightening, tissue closure site preparation is required in addition to suture fixation. A device that facilitates remote tissue site preparation for healing and reliable suture mediated site closure could offer a substantial improvement to the therapeutic options for many patients.

Another example of the need for better technology for remote tissue cutting and closing is evident from the fact that currently many patients still often require more extensive and dangerous surgery to remove certain intestinal lesions (e.g., abnormal growths, like polyps) that extend deeper than the superficial layer lining the intestine. Many superficial intestinal lesions reached using standard intestinal endoscopy equipment and techniques can be routinely completely removed endoscopically from the intestinal wall using a wire snare. Because of the lack of effective technology and techniques, typical deeper lesions cannot yet be safely removed using this non-surgical approach.

Patients who present with larger or deeper potentially intra-mural intestinal lesions usually would benefit from having part of the intestinal wall immediately adjacent to the base of the lesion also removed with the lesion. While removing some of the surrounding normal intestinal tissue can ensure that the lesion is more adequately removed, the risk of harvest site leakage or impaired wound healing substantially increases if the wound is not adequately closed. Currently available technology fails to provide a safe and reliable option for the completely endoscopic removal of deep-seated internal pathologic lesions. This second preferred embodiment holds promise for eliminating the need for some patients to have to go to the surgical operating room instead of just finishing the endoscopy in the endoscopy suite with the safe and complete removal of these deeper lesions.

To provide better patient outcomes, improved technologies are needed to continue to reduce the invasiveness and potential morbidity of opening and closing holes remotely made inside of patients. While the ability to remotely cut or open and close the walls of tubular tissue structures along with the use of translumenal therapeutic interventions offer exciting potential improvements to patient care, excellent technology is needed to make this promising opportunity into clinical reality. This innovation represents a significantly means to help a broader population of patients.

BRIEF SUMMARY OF THE INVENTION

Briefly stated and in accordance with both presently preferred embodiments of the invention: a therapeutic instrument for the ergonomic, effective and safe opening and closing of targeted remote tissue sites; includes a pistol grip style handle with a hand activated lever for needle deployment and, optionally, with features to control tissue cutting and guide wire installation; also incorporates a specialized elongated rigid or flexible instrument shaft, which enables vacuum assisted holding of tissue at a uniquely contoured distal tip, where placement of a suture in a purse string configures occurs along with, if desired, tissue cutting and guide wire passage.

In accordance with first preferred embodiment of this invention used for providing safe and reliable transmural access, this instrument enables creation of closeable transmural access sites by utilizing the special features disclosed herein: This innovation provides for vacuum mediated tissue manipulation and holding across multiple specially contoured gaps, which also support the simultaneous traverse of two needles that pick-up and retract back both ends of a single strand of suture configured to create a purse string suture arrangement in that tissue. The tissue is cut with a blade oriented perpendicular to the tissue held in the jaw and pulled toward the handle along the long axis of the distal tip. This incision is located appropriately between the purse string stitches. A guide wire can be passed through this incised tissue opening within the purse string suture to enable subsequent instrument passage over the guide wire through the transmural access point and into the extralumenal location. Upon completion of the intervention, after the device, guide wire and any other instruments are removed form the patient, the suture is drawn tight and secured to close the hole.

In accordance with another aspect, this invention provides a novel approach to stimulate wound healing by cutting and closing the wall of the tubular tissue structure (without necessarily removing any tissue or using the site for access) has potential for therapeutic interventions, called "plications," in which increasing tissue thickness or tissue tightening is advantageous. For example, a durable esophageal plication thickening and tighten tissue at the distal esophagus may reduce the risk of stomach contents from refluxing up from the stomach into the esophagus. Symptoms of gastric reflux range from mild heart burn to obstruction from esophageal cancer. Just placing stitches in the distal esophagus leads to temporary amelioration of reflux while the stitches remain in place to tip the balance towards supporting an effective anti-reflux mechanism. Without healing the stitches typically fall out within weeks or months. With healing at the site, the bulked up region of the esophagus can act as a permanent pressure valve against reflux.

In accordance with this additional example clinical application of the first embodiment of this invention, a similar ergonomic device that provides for effective remote tissue plication (tissue thickening and tightening) but does not require all of the innovative features used in creating transmural access sites. The instrument for tissue plication uses the aforementioned vacuum held multiple jaw positioned tissue, double needles for pick-up of ferrules attached to a single suture and the vertical blade longitudinal incision, but for this plication usage does not require guide wire passage. The incision prepares the wound site for long-term healing by exposing underlying tissue, while the purse string suture holds the tissue to thicken and tighten it during healing.

In accordance with the second preferred embodiment of this invention, a similar ergonomic device that enables the safe removal of remote tissue samples including parts of the adjacent tissue wall. Like the first preferred embodiment, this second embodiment uses vacuum to hold tissue in a customized orientation and a double needle and ferrules with a single strand to create a purse string suture placement. However, instead of a vertical blade, this second embodiment uses a horizontal oriented blade moving longitudinally towards the handle to amputate a lesion along with some of the adjacent tissue wall off of the targeted site. The use if a guide wire is not anticipated in this application. Securing the purse string suture closes the site.

A second embodiment of this invention can be used to safely and efficiently remove part of the wall of a hollow tissue structure along with an abnormal tissue growth attached to that part of the wall. Limitations in currently available intestinal endoscopy equipment force the need to have deep-seated lesions, which may extend into the adjacent wall (i.e., intramural), removed by a subsequent surgical procedure in the operating room instead of at the time of their evaluation in the endoscopy suite.

BRIEF DESCRIPTION OF THE SEVERAL VIEWS OF THE DRAWING(S)

The foregoing objects, features and advantages of the invention will become more apparent from a reading of the following description in connection with the accompanying drawings, in which:

FIGS. 6A and 6B are perspective views of the vacuum assisted tissue manipulation components of FIG. 3;

Figure 1:
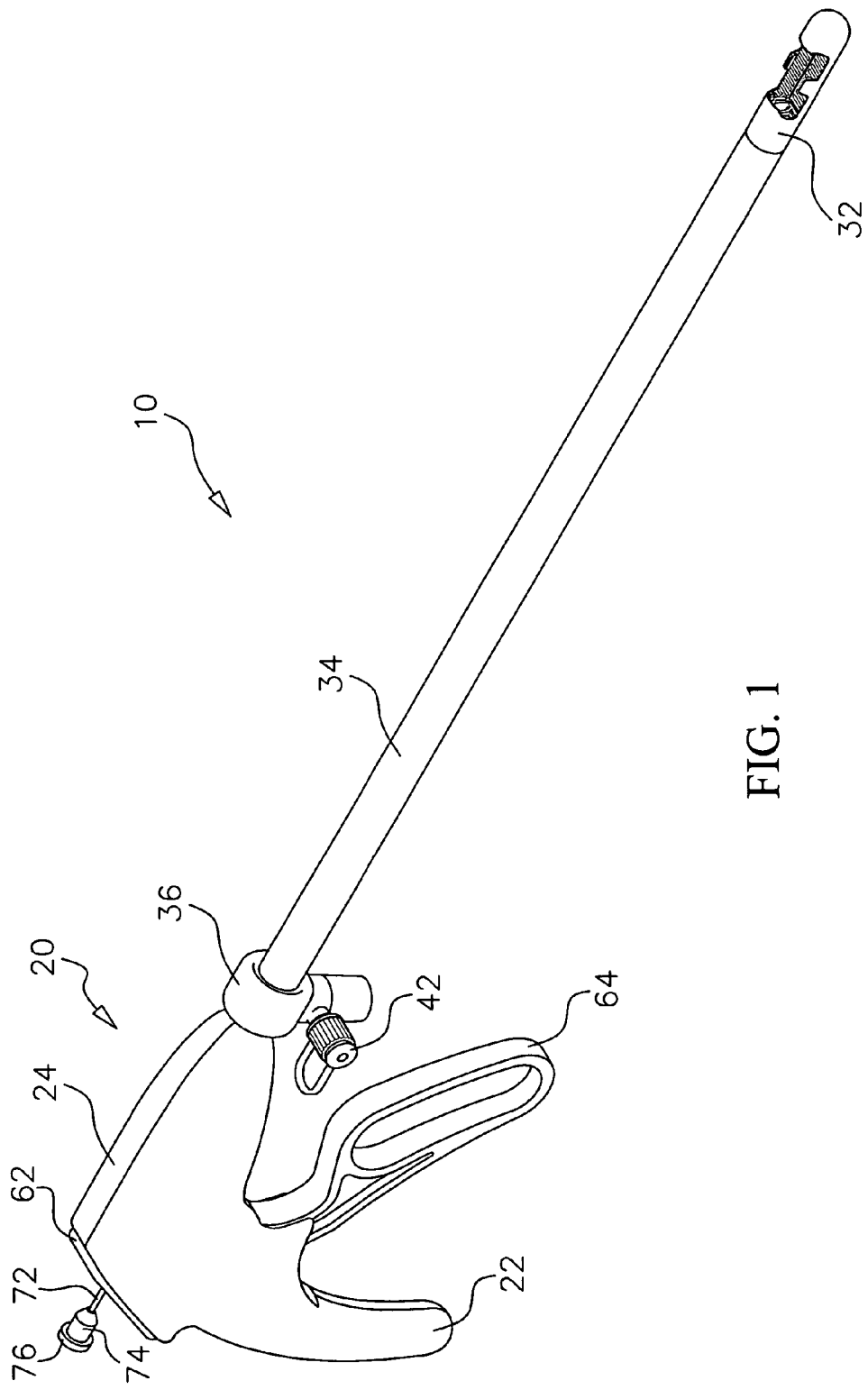
FIG. 1 is a perspective view of the tissue suturing instrument in accordance with the first embodiment of the present invention.
Figure 3:
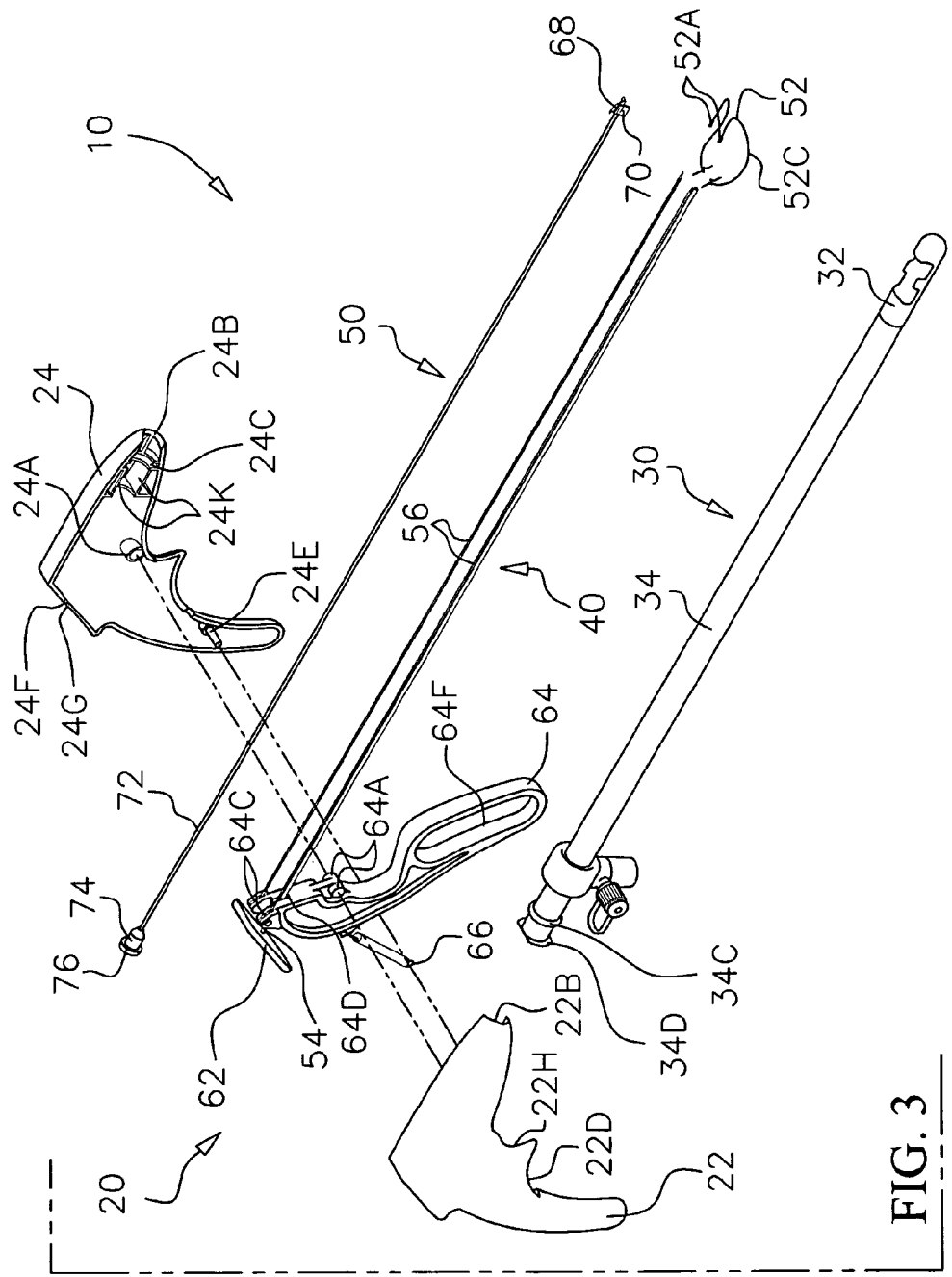
FIG. 3 is a partially exploded perspective view of the tissue suturing instrument of FIG. 1 in which the handle halves are separated highlighting the functional components for vacuum augmented tissue manipulation, purse string suture placement, tissue cutting and guide wire installation.
Figure 7B:
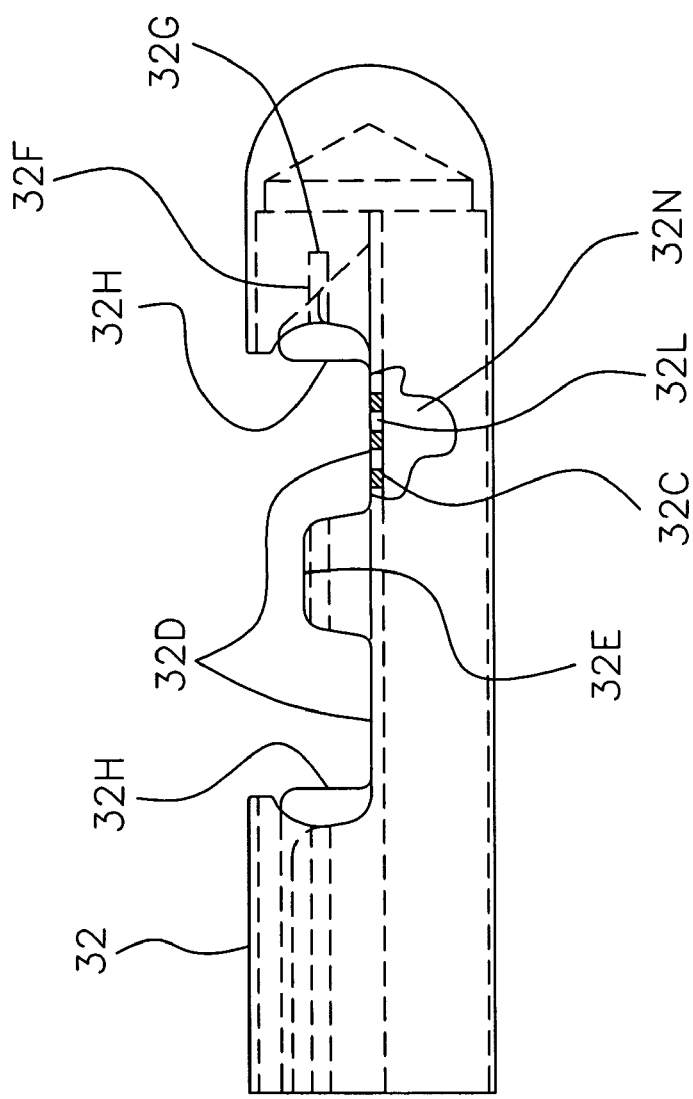
Figure 7A:
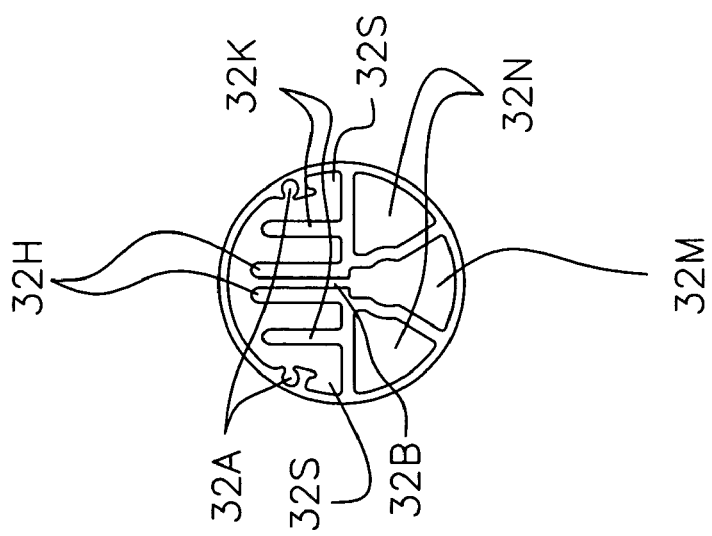
Figures 13A, 13B:
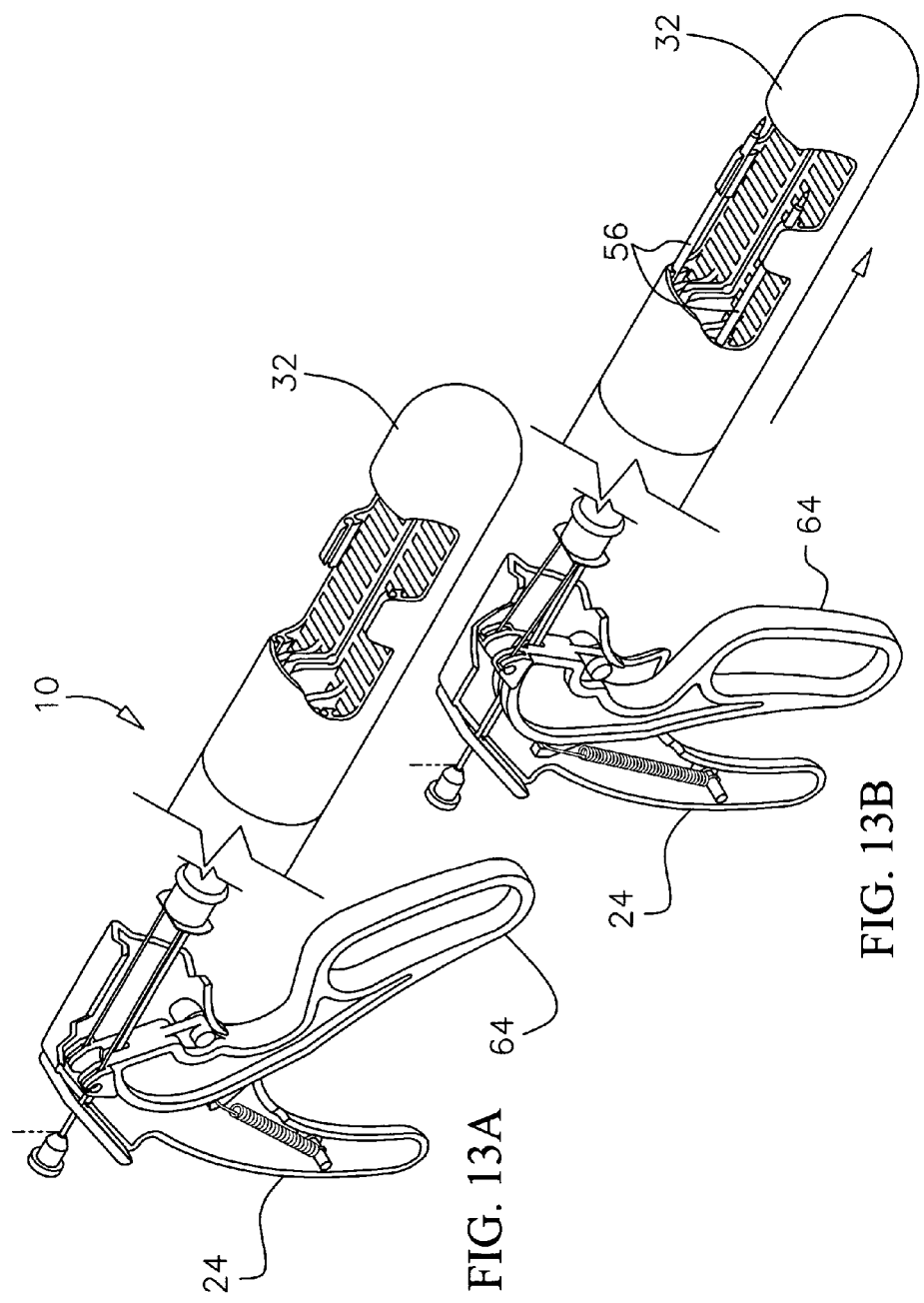
Figures 13E, 13F:
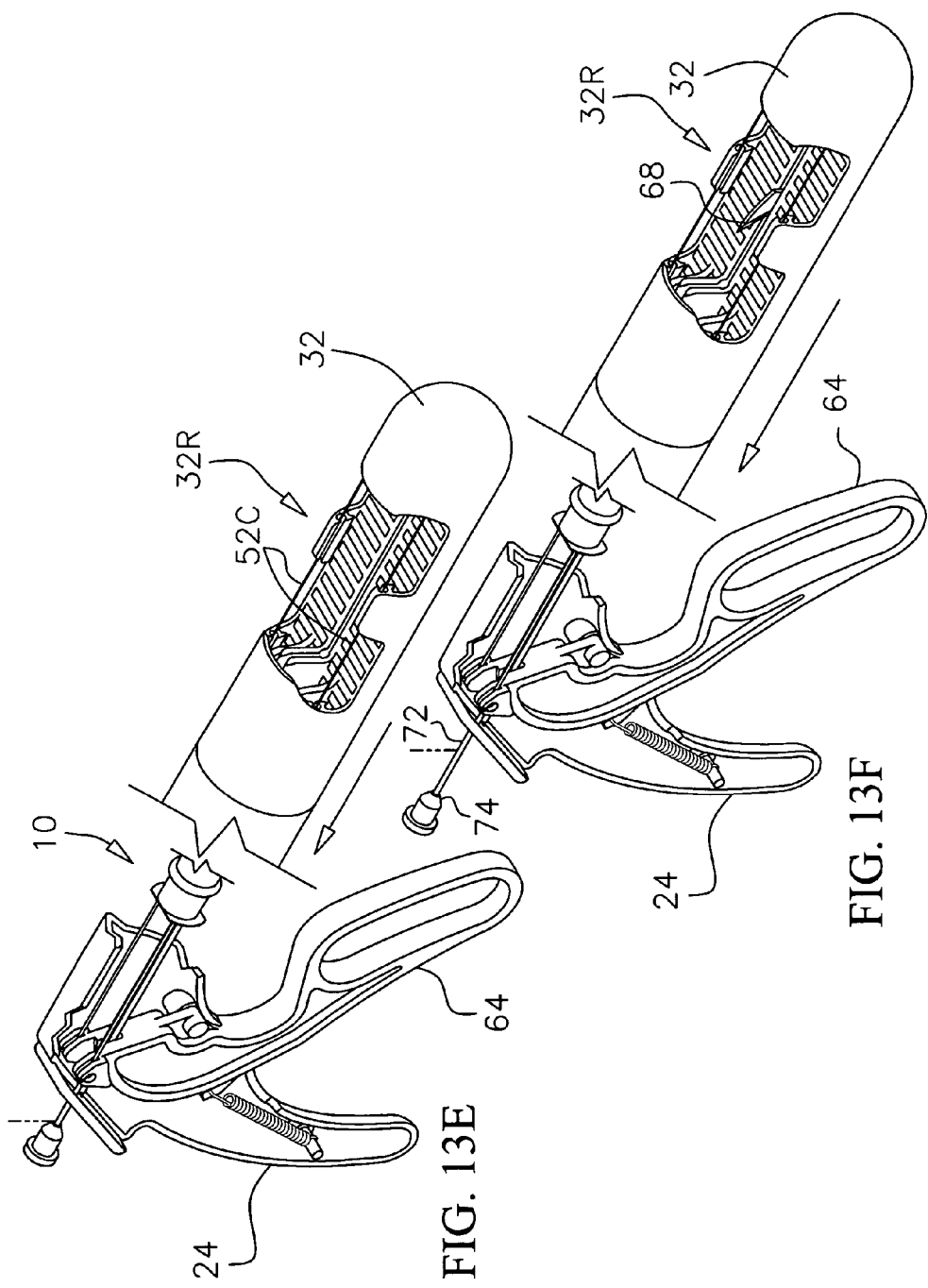
Figure 13G:
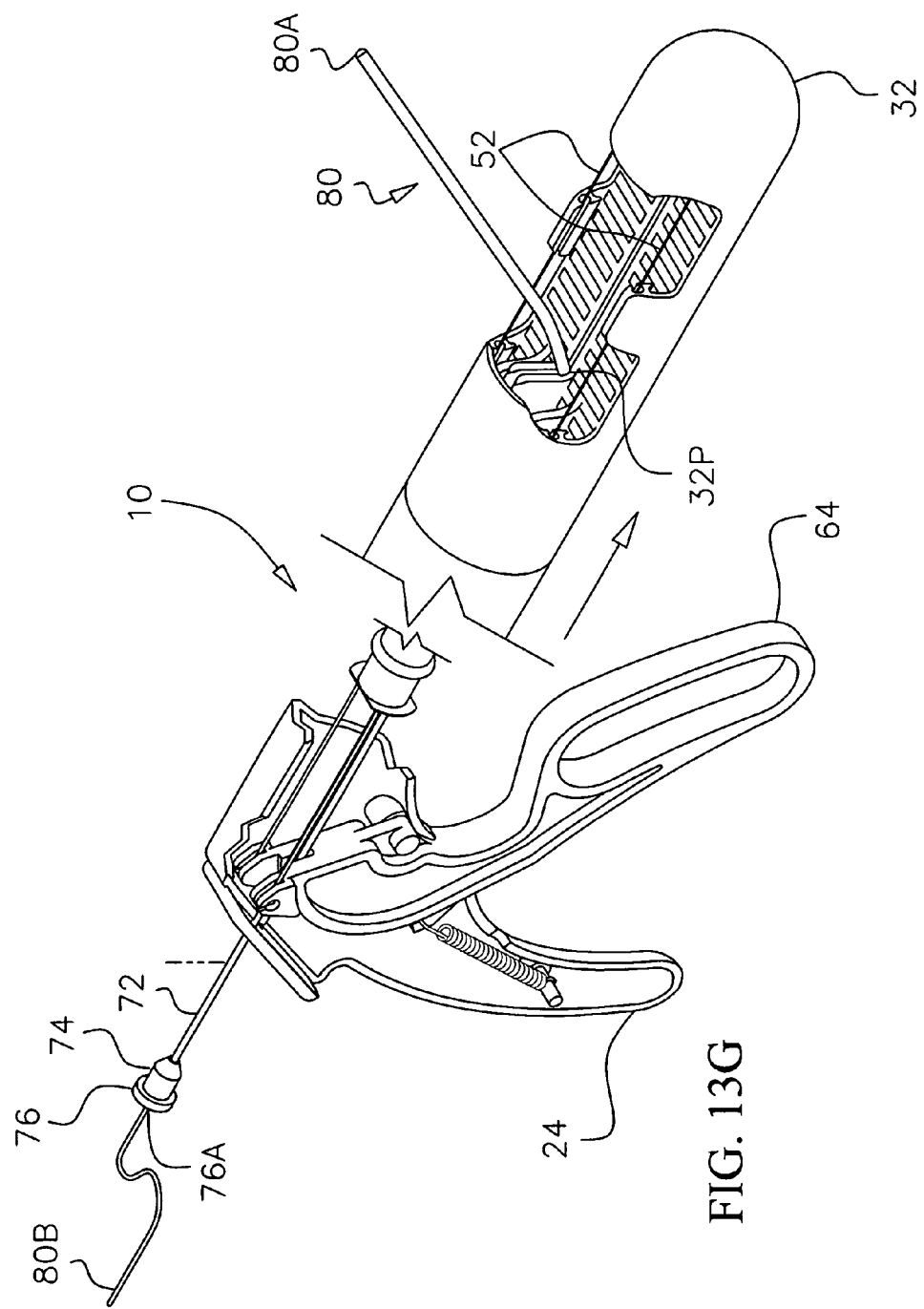
Figure 14:
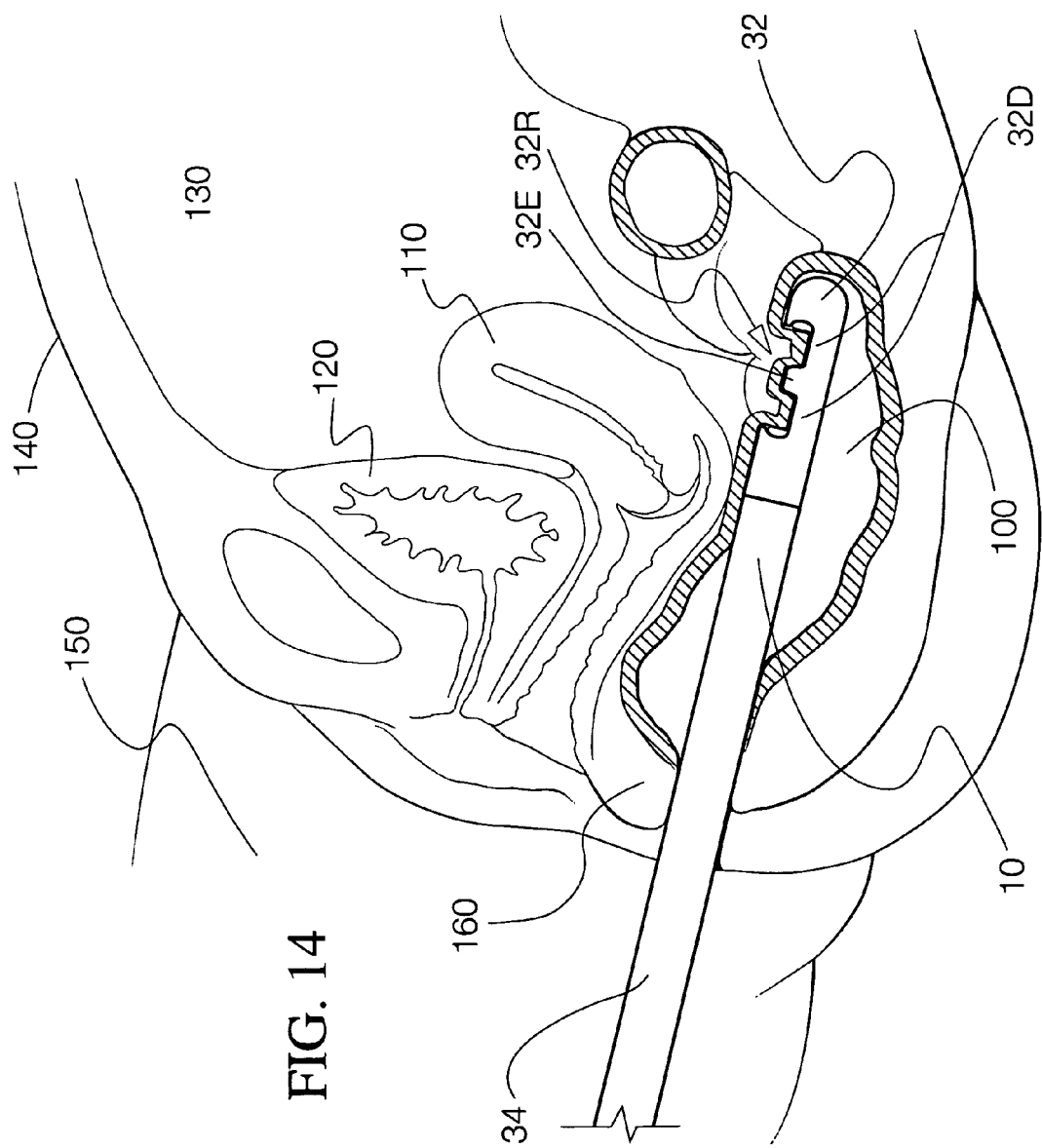
Figure 16:
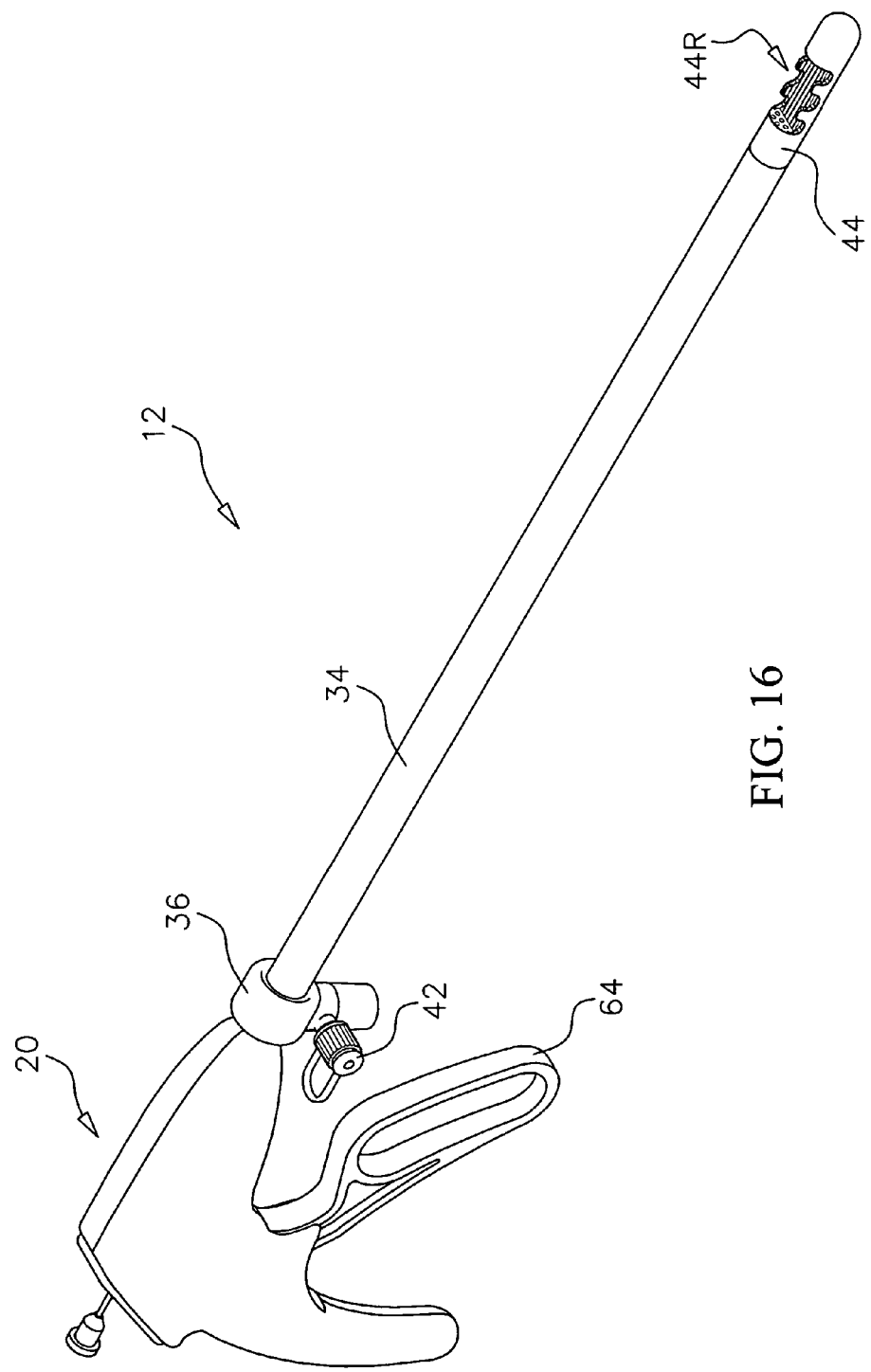

FIGS. 7A and 7B shown end view and a cross sectional view, respectively, of the distal vacuum tip of FIG. 3;

FIG. 8A is an perspective view highlighting the needle drive components of FIG. 3;

FIGS. 8B and 8C are perspective views of the proximal and distal ends, respectively, of the needle of FIG. 3;

FIG. 9A is an perspective view showing the suture storage features of FIG. 3;

FIG. 9B shows the ferrules at each end of a single strand of suture of FIG. 3;

FIGS. 9C and 9D show a perspective views of a needle next to a cross sectional view of a ferrule and another perspective view of a needle engaged within a cross sectional view of a ferrule, respectively;

FIG. 10A is a perspective view of the tell-tale suture loops held in the suture storage indicator and of the relative of the location of the ferrules held in the ferrule compartments at the distal side of the distal tip of FIG. 1;

FIG. 10B is a perspective view of the tell-tale suture loops now partially straightened out in the suture storage indicator and of the relative location of the ferrules now brought back to the proximal side of the distal tip of FIG. 1;

FIG. 11A is a perspective view of the tissue cutting components instrument of FIG. 1 showing the tissue cutter knob fully forward;

FIG. 11B is a perspective view of the tissue cutting blade and shuttle components on the blade tube of the instrument of FIG. 11A;

FIG. 11C is a perspective view of the tissue cutting components instrument of FIG. 1 showing the tissue cutter knob about half way pulled back and the cutting blade near the middle of the tissue manifold;

FIG. 11D is a perspective view of the tissue cutting blade and shuttle components on the blade tube of the instrument of FIG. 11A highlighting the shuttle's location relative to the distal end of the device;

FIG. 11E is a perspective view of the tissue cutting and guide wire placement components instrument of FIG. 1 showing the tissue cutter knob fully back and a guide wire partially inserted through the shuttle tube;

FIG. 11F is a perspective view of the tissue cutting blade and shuttle components on the blade tube of the instrument of FIG. 11A showing the blade shuttle fully retracted and the guide wire protruding through the curved distal portion of the shuttle tube;

FIG. 12A-12E show end views and cross section views of various blade shuttle components of the instrument of FIG. 3;

FIG. 13A is a perspective view of the instrument of FIG. 1 with the right handle housing removed and the distal tip magnified to show the lever fully forward and the needle tips not extending into the jaw;

FIG. 13B is a perspective view of the instrument of FIG. 1 with the right handle housing removed and the distal tip magnified to show the lever partially rotated back and the needle tips now extending into the jaws;

FIG. 13C is a perspective view of the instrument of FIG. 1 with the right handle housing removed and the distal tip magnified to show the lever fully rotated back and the needles fully forward through the jaw;

FIG. 13D is a perspective view of the instrument of FIG. 1 with the right handle housing removed and the distal tip magnified to show the lever partially released and the needles along with the attached suture ends traversing back through the jaw;

FIG. 13E is a perspective view of the instrument of FIG. 1 with the right handle housing removed and the distal tip magnified to show the lever fully forward back into its initial position and the needles and suture ends fully back to the proximal side of the jaw;

FIG. 13F is a perspective view of the instrument of FIG. 1 with the right handle housing removed and the distal tip magnified highlighting the blade knob and blade partially pulled back;

FIG. 13G is a perspective view of the instrument of FIG. 1 with the right handle housing removed and the distal tip magnified highlighting the blade knob and blade fully pulled back and a guide wire partially in place;

FIG. 14 is a schematic perspective view of the tissue suturing instrument of FIG. 1 shown in a transanal application;

FIG. 15A is a perspective view of the distal end of the instrument of FIG. 1 and a schematic representation of a tubular tissue;

FIG. 15B is a perspective view of the distal end of the instrument of FIG. 1 shown inserted into the lumen of the tubular tissue structure;

FIG. 15C is a perspective view of the distal end of the instrument of FIG. 1 with a segment of the tissue sucked into the jaws of the distal tip;

FIG. 15D is a perspective view of the distal end of the instrument of FIG. 1 with a segment of the tissue sucked into the jaws of the distal tip and the needles partially advanced through the tissue over the proximal manifold;

FIG. 15E is a perspective view of the distal end of the instrument of FIG. 1 with the needles fully advanced above the tissue proximal and distal jaws, but under the tissue between the jaws;

FIG. 15F is a perspective view of the distal end of the instrument of FIG. 1 showing the suture coming back over the tissue in the proximal and distal jaws but under the tissue in area between the jaws;

FIG. 15G is a perspective view of the distal end of the instrument of FIG. 1 showing a purse string suture placed around a segment of the tissue sucked into the jaws and the tissue cutting blade pulled back partially cutting the tissue held against the manifold;

FIG. 15H is a perspective view of the distal end of the instrument of FIG. 1 showing a purse string suture placed around a segment of the tissue sucked into the jaws and the tissue cutting blade pulled fully back into the instrument shaft to provide an incision in the tissue held in the manifold;

FIG. 15J is a perspective view of the distal end of the instrument of FIG. 1 inside of a tubular tissue structure showing a guide wire advancing through the incision in the tissue held in the manifold;

FIG. 15K is a perspective view of the distal end of the instrument of FIG. 1 pulled out of the tubular tissue structure leaving a purse string suture in place around an incision with a guide wire passed through it;

FIG. 15L is a perspective view of the tubular tissue structure with an incision circumscribed with a purse string suture and containing a guide wire over which a endoscope is passed;

FIG. 15M is a perspective view of the tubular tissue structure with an incision circumscribed with a purse string suture after the guide wire and instruments are removed;

FIG. 15N is a perspective view of the tubular tissue structure with an incision now drawn closed by placing tension on the ends of the purse string suture;

FIG. 15P is a perspective view of the tubular tissue structure with an incision now drawn closed by the tightened purse string suture over which a suture fastener and cutting device is passed;

FIG. 15R is a close-up perspective view of the tubular tissue structure with an incision now secured closed by purse string suture held in place with a mechanical fastener and the extra suture material trimmed away after the suture fastener instrument and trimmed suture ends are removed;

FIG. 16 is a perspective view of the second preferred embodiment of this invention;

FIG. 17A is a partial section view of the distal end of the instrument of FIG. 16 showing the needle and ferrule with suture along with the horizontal cutting blade. FIG. 17B is a section view through A-A of FIG. 17A.

FIG. 17C is a section view through B-B of FIG. 17A showing the horizontal cutting blade along with its attached pulling members from the instrument of FIG. 16.

FIGS. 18A, 18B and 18C show the distal end of the instrument of FIG. 16 with the needles partially advanced, the needles fully advanced with the horizontal blade partially pulled back and the needles fully advanced with the horizontal blade almost entering under the proximal vertical perforated wall, respectively.

Figure 20A:
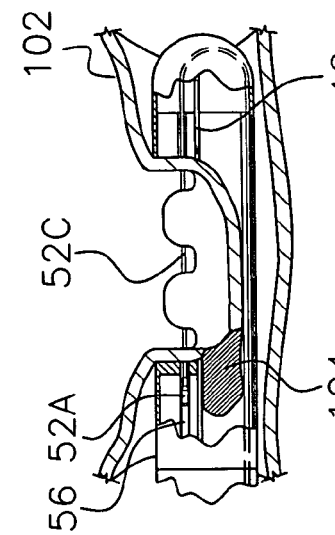
Figure 20B:
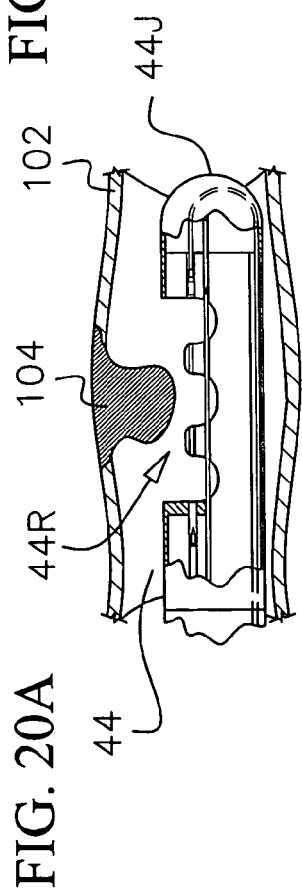
Figure 20C:
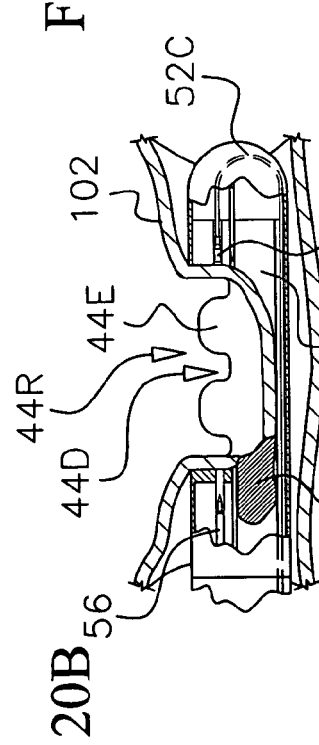
Figure 20D:
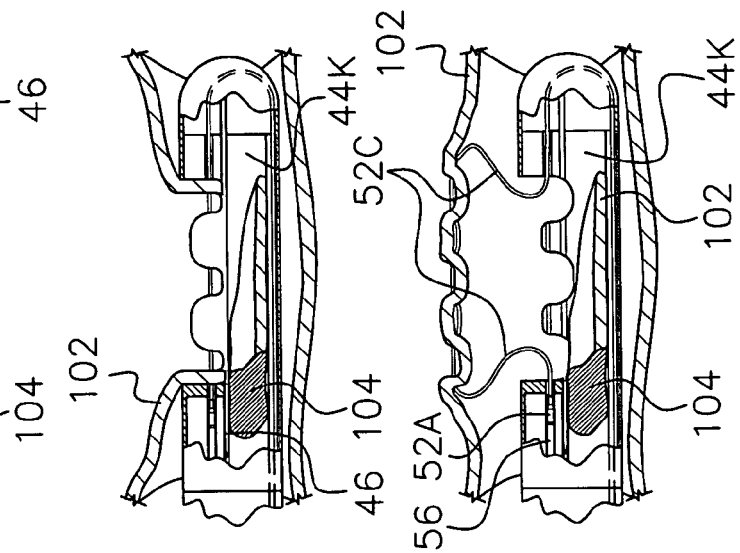
Figure 20E:
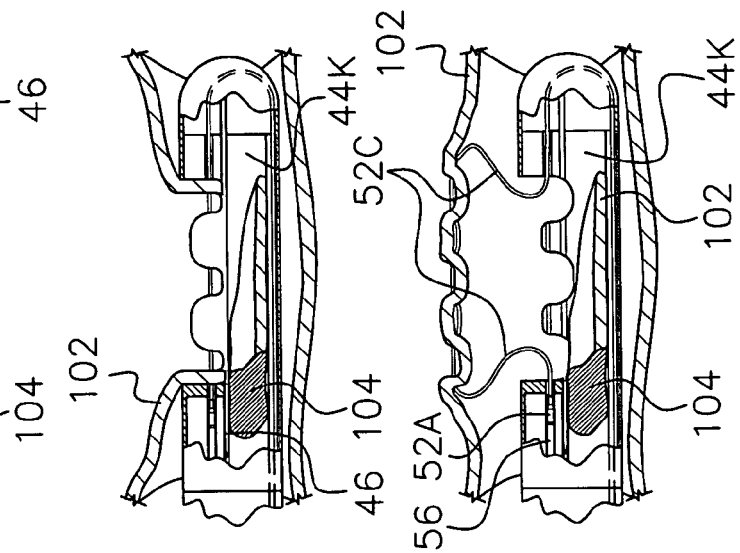
Figure 20F:
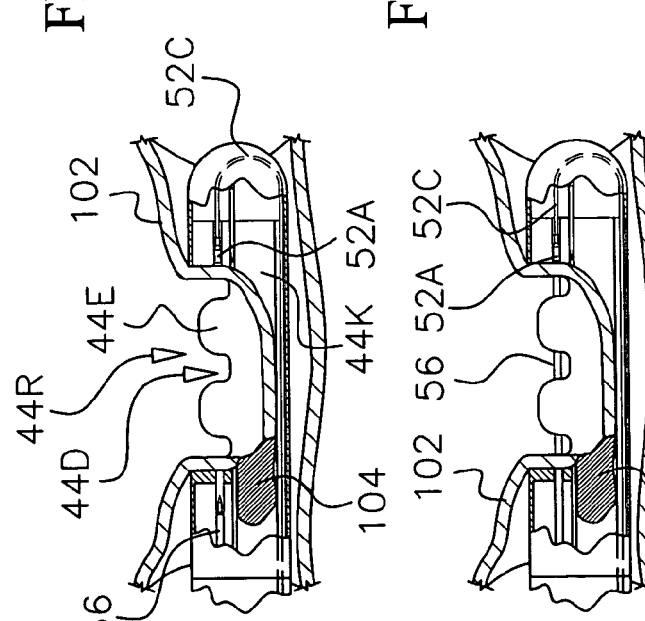

FIG. 19 shows perspective view of the distal end of the instrument of FIG. 16 with a partial cut-away to illustrate how this instrument engages a lesion attached to the wall of a tubular tissue structure;

FIG. 20A shows the distal end of the instrument of FIG. 16 inside of a tubular tissue structure containing a lesion;

FIG. 20B shows the distal end of the instrument of FIG. 16 inside of a tubular tissue structure now engaging the lesion within the opening in the distal end of the instrument;

FIG. 20C shows the distal end of the instrument of FIG. 16 inside of a tubular tissue structure, engaging the polyp with the needles fully advanced;

FIG. 20D shows the distal end of the instrument of FIG. 16 inside of a tubular tissue structure, engaging the polyp and the needles and ferrules with suture fully retracted;

FIG. 20E shows the distal end of the instrument of FIG. 16 inside of a tubular tissue structure, engaging the lesion with the needles fully retracted and the purse string suture in place around the base of the polyp and the horizontal blade fully excising the lesion's base from the wall of the tubular tissue structure;

FIG. 20F shows the distal end of the instrument of FIG. 16 now released from the inside of a tubular tissue structure with the purse string suture in place and the lesion secured within the distal opening;

DETAILED DESCRIPTION OF THE INVENTION

In accordance with the presently preferred embodiments of the invention, medical therapeutic instruments are provided for the ergonomic, effective and safe creation of transmural access sites, effective tissue plication and harvesting deep-seated remote tissue samples. Each instrument includes a pistol grip style handle with a hand activated lever, a specialized vacuum tissue manipulation feature at the end of the instrument shaft and a double needle mechanism for engaging ferrules attached to the ends of a single strand of suture to stitch a purse string suture configuration. These embodiments vary regarding the availability of specific customized features for tissue incisions and guide wire passage. First, the first preferred embodiment is covered in this detailed description for use in providing transmural access. Next, the use of this first preferred embodiment for creating tissue plication is addressed. Last, the second preferred embodiment is presented for use in harvesting deep-seated remote lesions. For clarity, these novel design features will be presented here in the sequence that they are typically encountered in these example procedures.

FIG. 1 is a perspective view of a tissue suturing instrument in accordance with the first embodiment of the present invention instrument 10. A handle assembly is constructed from a right handle portion 22 and a left handle portion 24 which are constructed of an injection molded plastic or the like and to which subsequent components are attached. An elongated body 34 extends from the handle to a distal end at which a tip 32 is located. A suction fitting 36 is disposed on the proximal end of body 34 and is preferably rotatable with respect to the body. A removable cap 42 is attached to a neck of the suction fitting 36.

Preferably the handle 24 has a window 62 described in more detail below. A cutter control knob 74 is attached to a cutter shaft tube 72 extending rearwardly from the handle.

The first preferred embodiment of this invention, suturing instrument 10, is represented in FIGS. 1-15P. Now referring to FIGS. 1-4, the illustrated suturing technique using needles and suture attached to ferrules of instrument 10 may be similar to that shown in U.S. Pat. Nos. 5,431,666, 5,766,183, 6,997,931 B2, European Patent No. EP 0669101, filed Feb. 23, 1995 and granted Oct. 14, 1998, which are incorporated by reference in the SEW-RIGHT® SR.5® and Running Device® and ESD™ products manufactured by LSI SOLUTIONS, Inc. (formerly LaserSurge, Inc.) of Victor, N.Y.

The innovation of the present invention is the unique combination of simultaneously firing two needles through a tissue gap in a pleat formed in the tissue by the instrument incorporating customized contours in the distal tip 32 to enable the needles to create a purse string suture configuration by parallel needles entering and exiting the tissue multiple times in a single traverse. This surgical purse string suture configuration resembles the purse string or draw string at the top of a soft sided purse and offers a similar function. It is a single suture sewn into and out of the tissue circumscribing the selected site. The final stitch exits the tissue near the entry point of the first stitch so that the surrounded site is drawn closed when tension is placed on both ends of the suture. This technology further utilizes vacuum conveyed through a housing 36 to hold the tissue and a specialized blade shuttle connected to a funnel knob 74 to reliably cut the tissue and, when desired, permit the installation of a guide wire. As used herein, pleat is intended to refer to any configuration of tissue that permits the above described stitch to be placed.

Figure 2:
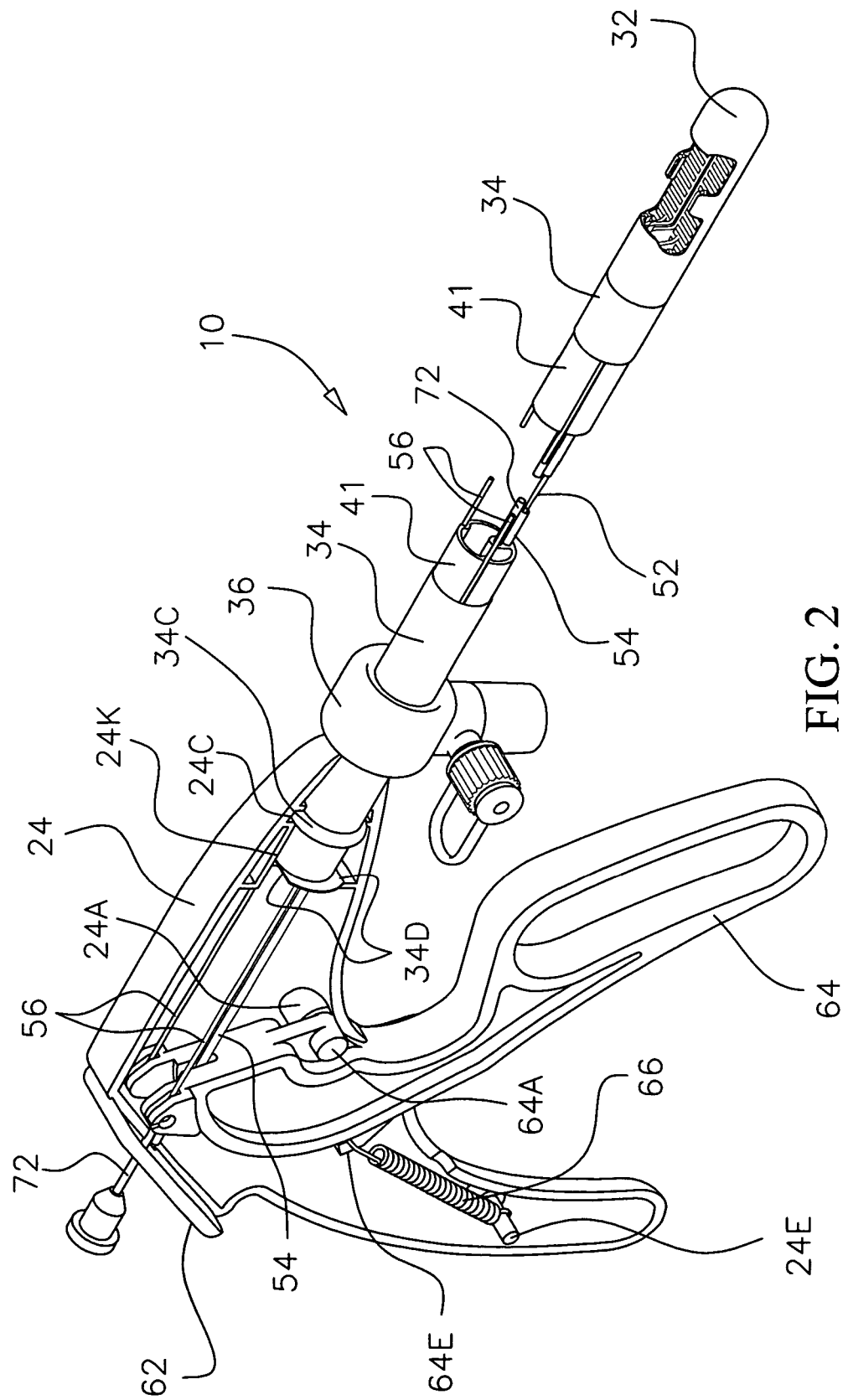
FIG. 2 is a perspective view of the tissue suturing instrument of FIG. 1 in which the right cover of the housing of the instrument is removed and sections of the shaft are removed to illustrate internal components.

FIG. 2 is a perspective view of the tissue suturing instrument of FIG. 1 in which the right cover of the housing of the instrument and sections of the shaft are removed to illustrate internal components.

Figure 4:
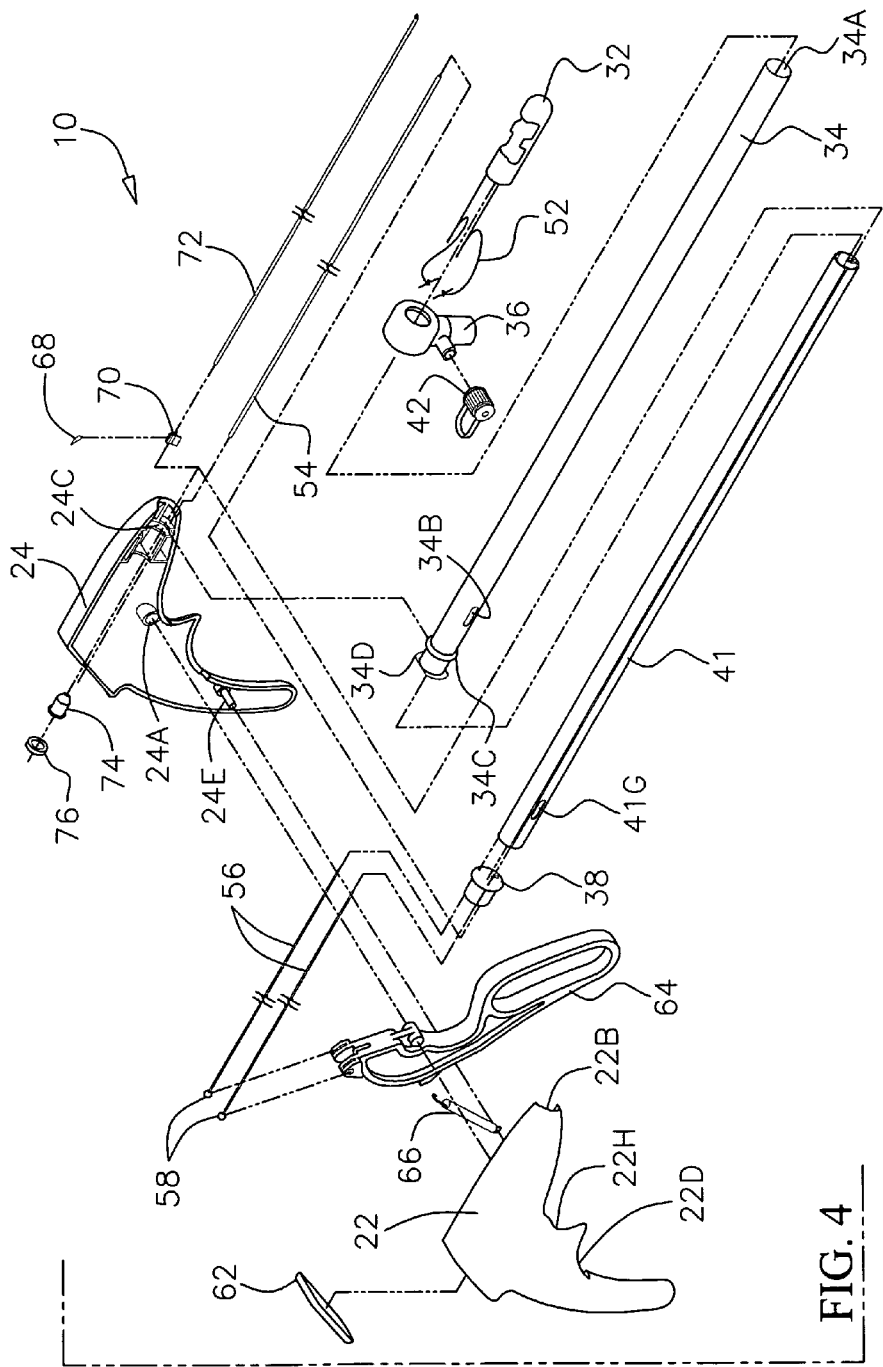
FIG. 4 is an exploded perspective view of the tissue suturing instrument of FIG. 1.

FIG. 3 is a partially exploded perspective view of the tissue suturing instrument of FIG. 1 in which the handle halves are separated highlighting the functional components for vacuum augmented tissue manipulation, pleat formation, purse string suture placement, tissue cutting, and guide wire installation. FIG. 4 is an exploded perspective view of the tissue suturing instrument of FIG. 1.

A lever 64 configured to be operated by the fingers of a user while grasping handle 20 provides for the extension and retraction of needles 56 of the instrument 10. Distally, a tube shaft 34, shown here as rigid, but which may also be flexible, protrudes from the handle assembly 20. The housing of the handle assembly 20 has a body shaped like a pistol having a handle portion made of a two-piece construction of molded plastic components 22 and 24. A pair of elongated needles 56 extends from housing 20 through the shaft 34 into the tissue-engaging tip 32. Each needle 56 has a non-tissue engaging end in the housing having a spherical member 58, such as a ball or bearing, attached thereto. Both needles 56 and spherical members 58 may be a made of metal, such as surgical stainless steel. The spherical member 58 may have a bore 58B into which the non-tissue engaging ends of the needles 56 extend and are joined thereto, such as by welding or brazing.

The suturing instrument 10 includes an actuator member 64 preferably in the form of a lever 64 having two pins 64A extending into holes 22A and 24A in the sides of housing 22 and 24 respectively, upon which pins the actuator member is pivotally mounted in the housing. Actuator member 64 extends through an opening 22D and 24D (FIGS. 3 and 4) in housing 20 to enable pivotal movement about pins 64A. An extension spring 66 is provided which hooks at one end in a notch 64E of actuator member 64 and is connected at the other end around a handle spring post 24E, which extends into a handle post receiving pocket located in the side of housings 24 and 22, respectively, such that the actuator member 64 is spring biased to retain actuator member 64 normally in a forward position, as shown for example in FIG. 1.

Ball sockets 64B are provided in the actuator member 64 which is shaped to received both of the non-engaging ends of needles 56, i.e., spherical members 58, to be driven forward by an operator pulling actuator member 64 to pivot actuator member 64 within lever openings 22D and 24D. Two slots 64C (FIG. 3) are provided for needle shafts 56D near the spherical members 58. An additional central slot 64D is also provided to allow free passage of suture tube 54 and cutter tube 72.

With its right handle half 22 shown removed and its left handle half 24 shown in place, FIG. 2 best illustrates the relationship between the handle housing 20 and the tube shaft 34. Note the slotted capture feature 24C in handle 24 engages the annular protruding capture feature 34C of tube shaft 34. The partially exploded view of FIG. 3 further reveals the anti-rotation feature 34D of tube shaft 34 which is constrained by the corresponding pocket 24K of handle 24. At its interface with handle assembly 20, tube shaft 34 exits through hole 22B and 24B.

The partially exploded perspective view of FIG. 3 highlights the major functional elements of the tissue suturing instrument 10, which include the handle assembly 20, a vacuum assembly 30, a needle drive and suture storage assembly 40, and a tissue cutting shuttle assembly 50, which enable tissue incision and guide wire installation. A clear plastic suture-viewing window 62 is shown in position relative to lever 64 and to suture tube 54.

FIG. 4 is a fully exploded perspective view of the tissue suturing instrument 10 showing its right handle portion 22, left handle portion 24, needle actuating lever 64, and its spring 66. The disassembled tube shaft assembly 30 is comprised, from distal to proximal, of a distal tip 32, tube shaft 34, a needle guide 40, a vacuum housing 36, a vacuum seal 38. Also contained therein, as shown in the breakaway in FIG. 2, are the needles 56, suture tube 54 with its suture 52, along with cutter tube 72 attached at its distal end to blade shuttle or follower 70 and its integrated blade 68 and, at its proximal end 72D, to funnel knob 74 capped by guide wire seal 76.

Figure 5:
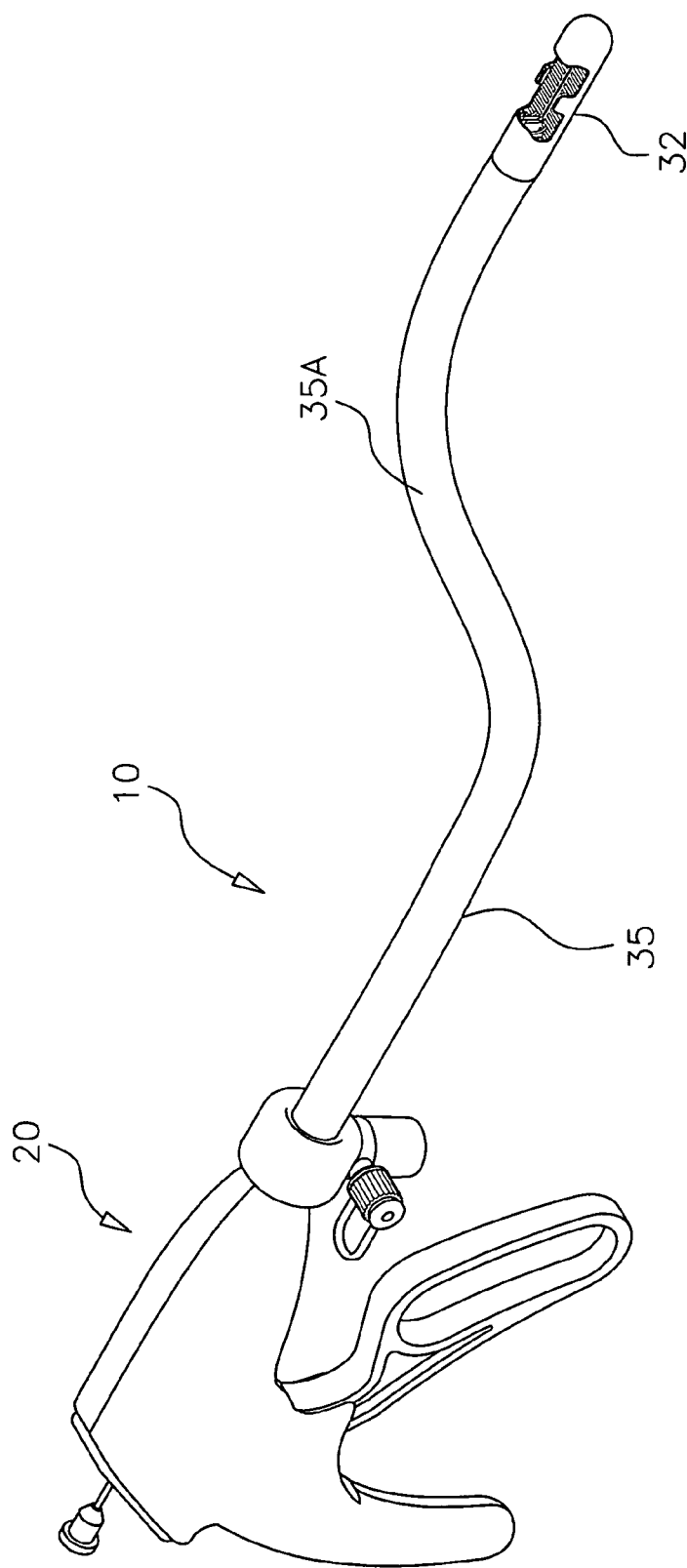
FIG. 5 is a perspective view of the tissue suturing instrument of FIG. 1 showing a curved or flexible shaft.

FIG. 5 is a perspective view of the instrument 10 now shown having a tube shaft 35 that is bent, flexible, malleable or steer able as indicated at the curved section 35A near the middle of the shaft. A non-straight or non-rigid shaft enables access to many potentially clinically relevant sites that are not reachable by straight or rigid instruments.

FIGS. 6A, 6B, 7A and 7B present the vacuum mediated tissue positioning function of this first preferred embodiment. FIG. 6A is a sectioned partially exploded view of the vacuum features of tube shaft 34. FIG. 6B is a slightly enlarged (relative to FIG. 6A) perspective view of distal tip 32. Vacuum is applied through attaching a tube connected to a negative pressure source at the hose connector 36D of rotational housing 36 (previously first described in U.S. Pat. No. 6,997,931 B2). This housing has an additional port 36C, which is closed by cap 42. Communicating hole 36B in vacuum housing 36 facilitates transmission of vacuum between the vacuum source and the tube shaft 34 through the hole 34B. The lip seals 36A on either side of housing 36 prevents vacuum leakage even during rotation of the vacuum housing 36 about tube shaft 34. Communicating hole 40G of needle guide 40 transmits vacuum to the vacuum channel 40A of needle guide 40. Vacuum seal 38 has a compressible rim 38A which seals against the inside surface of capture feature 34C. This seal also prevents vacuum leakage around the needles 56 (not shown) at 38D and the shuttle tube 72 (not shown) at 38C and the suture tube 54 (not shown) at 38B.

The end view drawing on the left side of FIG. 7A shows features of distal tip 32 with a the continuous path for vacuum through channels 32N, which communicate with slots 32L located in the manifold bed 32C to ultimately draw tissue into contoured gaps 32D separated by septum 32E and down against manifold bed 32C to form a pleat in the tissue to enable purse string suture placement. Note the cut away shown beneath distal tissue gap 32D. Also note cut location features 32H, which controls cut length in tissue by setting the start and stop points of the cut. Tissue stop features 32K prevent tissue from being sucked into the proximal and distal ends of tissue gaps 32D. FIG. 7B also illustrates needle passages 32A, blade track 32B, shuttle track 32M and ferrule compartment 32F with ferrule stop 32G.

FIG. 6B is an isometric view of the features described above in FIG. 7. In addition, FIG. 6B well illustrates the guide wire exit hole 32P and the rounded end 32J of distal tip 32.

FIGS. 8A, 8B and 8C show the needle drive components. Many of the features in FIG. 8A have already been individually described. This illustration shows the relationship between the pivoting lever 64 with its two ball sockets 64B and needle slots 64C and the needles 56 as well as the needle track features 41D of the needle guide 41. FIG. 8B shows an enlarged view of a needle ball 58 with bearing surface 58A and a needle receiving opening 58B, which attaches to the proximal needle end 56E. FIG. 8C shows the distal needle end 56D, which connects to the distal tip of the needle where ferrule engagement occurs. Needle ferrule stop shoulder 56C is proximal to asymmetric ferrule snap feature 56B, which includes opposing relief sections 56F for engaging and releasing ferrules 52A (shown in FIGS. 9B and 9C) at the symmetrical annular ferrule snap 52B. As can be seen, the needle and section 56D has a larger diameter than the needle tip section. The ferrule snap feature 506B located proximate to the distal end of the needle has a dimension in one direction that is larger than a diameter of the adjacent needle section and a dimension in another direction, in this case orthogonal to the first direction smaller than the needle dimension. Preferably, the surface in the enlarged dimension is the rounded surface as indicated at 56B, while the surface in the other direction is a flat surface as indicated at 56F. A sharp pointed tip 56A, shown here in a conical shape, is located at the most distal end of needle 56.

FIG. 9C shows the asymmetric needle snap feature 56B engaging the symmetrical annular ferrule snap 52B to temporarily attach the needle 56 to the ferrule 52A. The opposing relief sections 56F of needle snap feature 56B permit release of ferrules 52A off of needle snap feature 56B by providing clearance for the tubular ferrule to temporarily deform into an oval shape and pass over the larger diameter needle snap feature 56B. It will be appreciated that the ferrule is at least somewhat resilient to permit to be deformed when the needle passes through the constricted portion defined by interior circumferential rib 52B. As can be seen, the rib 52B may be formed by deforming the sleeve inwardly at the location of the rib.

FIGS. 9A, 9Ba and 9C highlight the suture and suture storage of this embodiment. A complete suture set 52 is comprised of a single strand of suture 52C attached to two ferrules 52A, one at each end. Each ferrule 52A is held in its individual ferrule compartment 32F (see FIGS. 7A, 7B, 10A and 10B) with the attached suture 52C fed through the distal tip 32 within the suture tube 54 underneath blade shuttle 70. The suture 52C continues back within the suture tube 54 through the opening 41B in the needle guide 41. The suture tube 54 passes through the vacuum seal 38, enters the cavity within handle halves 22 and 24, traverses the lever slot 64D in lever 64 and the suture tube distal end 54B terminates into the opening described by the recesses 22G and 24G in handle halves 22 and 24, respectively.

The mid section of suture set 52 is arranged to indicate suture 52C payout achieved by successful pick-up of both ferrules 52A; this tell-tale safety feature demonstrates the pulling of both ferrules was described in U.S. Pat. No. 6,641, 592 B1. Tell-tale suture loops 52D are arranged immediately to the ferrule side of the mid point of the suture strand. When the suture 52C connected to each ferrule 52A is pulled toward the handle by the needles 56, these tell-tale loops 52D straighten out as an indicator of successful ferrule 52A pick-up.

FIG. 10A shows the arrangement and location through the clear window 62 of both tell-tale suture loops 52D separated by a septum composed of handle features 22J and 24J with both ferrules 52A remain held in their ferrule pockets 32F in the distal tip 32. FIG. 10B shows the appearance of the now straightened out tell-tale loops (pulled through handle channel composed of openings 22G and 24G) evident of needle 56 retraction of both ferrules 52A with their attached suture 52C. As used herein, and in the claims, clear and are transparent or exemplary and are meant to describe a window through which the suture portions 52D can be seen, and not to suggest that the window is clear or transparent in an optical sense.

FIGS. 11A-11F are perspective views of the tissue cutting and guide wire passage components 50 of instrument 10 of FIG. 1 as shown assembled in FIG. 3. Note the reference lines located at the proximal and distal ends of these drawings to help indicate the relative travel of the funnel knob 74 disposed on the proximal and of longitudinal blade actuator 72 and the blade shuttle 70 located on the distal end thereof, respectively. FIG. 11A shows the funnel knob fully forward. FIG. 11B shows the position of the blade shuttle 70 relative to the distal tip 32 of FIG. 11A.

FIG. 11C shows the cutter control funnel knob 74 back about halfway and the cutting blade 68 near the middle of the tissue manifold bed 32C. FIG. 11D shows the blade shuttle 70 relative to the distal tip 32 of FIG. 11C. FIG. 11E shows funnel knob 74 in the fully back position with the guide 80 passing through guide wire seal 76 and through shuttle tube 72. The distal end 80A of guide wire 80 exits in an upward orientation out of an upturned portion 72B of the shuttle tube 72 and a guide wire exit hole 32P at the proximal side of distal tip 32. FIG. 11F shows blade shuttle relative to the distal tip 32 of FIG. 11E and well illustrates the curved guide wire director 72B located at the distal end of the shuttle tube 72, where the guide wire 80 is diverted in the upward directed.

FIG. 12A-12E show end views and cross section views of the blade shuttle components of the instrument of FIG. 3. FIGS. 12A and 12B show a guide wire seal having a slit 76A acts as closed valve until it receives and seals around a guide wire 80 (not shown). Guide wire seal 76 includes a recessed pocket 76B to engage and seal on raised seal lip 74E at the proximal end of funnel knob 74, FIG. 12C. A tapered guide wire receiving aperture 74A communicates with a stepped longitudinal bore having a distal shoulder 74D for engaging the proximal end 72D of shuttle tube 72 and an enlarged shuttle tube receiving opening 74C within funnel knob 74, which is gripped and pulled by grasping surface 74B. FIG. 12D shows the proximal end 72D of shuttle tube 72, which can be attached to funnel tube opening 74C by means such as gluing or welding.

FIG. 12E shows that the distal end of shuttle tube 72 is received in opening 70B of blade shuttle 70, which also holds blade 68 in slot 70A thereof. Blade 68 can be attached to blade shuttle 70 by means such pinning, gluing or welding. The blade 68 incorporates a sharpened tip 68A and a sharpened curved cutting surface 68B. Blade shuttle 70 includes bearing surfaces 70C, which ride within corresponding features 32M of distal tip 32 as shown in the end of FIG. 7.

FIGS. 13A-13G are perspective views of the instrument of FIG. 1 with the right handle housing 22 removed and the distal tip 32 magnified relative to the rest of the drawing. These drawings highlight the needle-suture function along with the tissue cutting and guide wire passage features. FIG. 13A shows the lever 64 fully forward with the needles 56 (not visible) fully retracted and not extending into the tissue jaw 32R. FIG. 13B shows the lever 64 partially rotated back and the needles 56 now extending into the distal tissue receiving region 32D of tissue jaw 32R. FIG. 13C shows the lever 64 fully rotated back and the needles 56 fully forward through the tissue jaw 32R to fully engage both suture ferrules 52A (not visible).

FIG. 13D shows the lever 64 partially released and the needles 56 along with the engaged or picked-up ferrules 52A with their attached suture 52C traversing back through the tissue jaw 32R. FIG. 13E shows the lever 64 fully released in its forward position, and the needles 56 and suture 52C fully extending across tissue jaw 32R. FIG. 13F shows the blade knob 74 with its attached shuttle tube 72 and blade 68 partially pulled back into tissue receiving region of the jaw 32R. FIG. 13G shows the blade knob 74 with its attached shuttle tube 72 and blade 68 (not visible) now fully pulled back. The proximal end 80B of guide wire 80 is inserted into the guide wire opening 76A (not shown) through the guide wire seal 76 on the shuttle pull knob 74 attached to shuttle tube 72, through which tube the guide wire 80 passes until it exits the upturned, curved guide wire opening 32P in the distal tip 32. The distal tip 80A of guide wire 80 advances in an upward direction because of the curved feature 72D in the distal end of the shuttle tube 72, which are not visible in this drawing because they are internal features.

FIG. 14 is a schematic illustration of a sagittal cross section of a human female pelvis providing a perspective view of the surgical suturing instrument 10 shown in a transanal 160 application. The placement of the shaft 34 of the instrument 10 determines the location of the distal tip 32. The right leg 150 and anterior abdominal wall 140 are labeled at the top of the drawing. The bladder 120 and uterus 110 are in the peritoneal cavity 130 above the rectum 100. Tissue receiving gaps 32D and projection 32E in the tissue jaw 32R of distal tip 32 hold the rectal wall tissue in a pleated configuration in preparation for purse string suturing, tissue incision and guide wire passage. Use of this innovation is also beneficial in other tubular tissue structures, such as the vagina, esophagus, stomach, small intestine, cecum, the entire colon and even the urinary bladder.

FIGS. 15A-15R show a method in accordance with this invention for opening and closing a transmural access site. FIG. 15A is a perspective view of the distal end 32 of the instrument 10 and a schematic representation of a tubular tissue segment such as rectal tubular tissue 100. The arrow indicates the direction in which the rounded distal end 32J of the distal tip 32 will enter the inner space or lumen of rectal tissue structure 100. FIG. 15B is a perspective view of the rounded most distal end 32J now inserted into the lumen of the tubular tissue structure 100 and a hidden line representation of the remainder of the distal tip 32.

FIG. 15C shows a segment of the wall tissue sucked into the tissue receiving region of the jaw 32R of the distal tip 32 and contoured to form a pleat corresponding to the shape of the tissue gaps 32D and projecting tissue septum 32E. FIG. 15D shows both needles 56 partially advanced through the tissue over the manifold into the proximal tissue gap 32D; the arrow indicates the direction and length of the traverse of the needles 56. FIG. 15E shows the needles 56 fully advanced above the tissue held in the proximal and distal tissue gaps 32D, but through and under the tissue at the tissue septum 32E; the arrow indicates the direction and full length of the traverse of the needles 56. FIG. 15F shows ferrules 52A at each end of the attached suture 52C coming back over the tissue in the proximal and distal tissue gaps 32D but under the tissue at tissue septum 32E; this suture placement creates a purse string configuration. The operator can now see through window 62 that the tell-tale suture loops have straightened out (FIGS. 10A-10B) to ensure effective suture pick-up. If either tell-tale suture loop remains looped, satisfactory suture pick-up may not have occurred. Prior to cutting any tissue, the operator can remove the device and suture from the patient, view the targeted site again and determine if another transmural attempt should be made.

FIG. 15G shows the tissue cutting blade 68 pulled back partially cutting the tissue 100 held against the manifold bed between the a purse string suture 52 placed within the segment of the tissue sucked against the manifold bed 32C of the jaw 32R. FIG. 15H shows a completed incision 101 in the tissue held against the manifold bed 32C in the tissue jaw 32R; note the vertical incision seen at the proximal cut location feature 32H. FIG. 15J shows a guide wire 80 advancing through the incision 101 in the tissue held in the tissue jaw 32R. FIG. 15K shows the instrument 10 pulled out of the rectal tubular tissue structure 100 leaving a purse string suture 52 in place around an incision 101 with a guide wire 80 also left in place through the incision 101. FIG. 15L shows the incision 101 circumscribed with a purse string suture 52 and containing the guide wire 80 over which an endoscope 85 is passed to complete the desired procedure.

FIG. 15M shows the rectal tubular tissue structure 100 with its incision 101 circumscribed with a purse string suture 52 after the guide wire 80 and all other instruments are removed. FIG. 15N shows the tubular tissue structure 100 with its incision 101 now drawn closed by placing tension on the ends of the purse string suture 52. FIG. 15P shows a suture fastener 91 installed in the tip of the suture fastening and cutting device 90 being passed along this suture toward the purse string closure site. FIG. 15R is a close-up perspective view from the inside of the tubular tissue structure 100 with the incision 101 now secured closed by purse string suture 52C held in place with a mechanical fastener 91 and the extra suture material trimmed away. The suture fastener instrument 90 and trimmed suture ends are already removed.

The creation of durable tissue plications, an additional example application of this first preferred embodiment, can also be explained using FIGS. 15A-15R. Similar to using this first preferred embodiment Oust reviewed) for opening and closing a transmural access site, the construction of a long-lasting thickening and tightening plication can be achieved with the same instrument 10 minus utilization of the guide wire passage features. Referring now to FIGS. 13A-13B of instrument 10 of FIG. 1, the instrument distal tip 32 is passed through a natural orifice and positioned at an appropriate location in a tubular tissue structure. Instead of the tubular tissue structure 100 representing the rectum as in the above example, for this example, assume the same tubular tissue structure 100 now represents the distal esophagus. The instrument 10 is now proportionally smaller than the previously described instrument 10 since the esophagus is usually smaller than the rectum.

FIG. 15C now represents the wall of the distal esophagus of tubular tissue 100 as it is drawn by vacuum into the tissue jaw 32R. FIGS. 13D-13F show the simultaneous traverse and retraction of both needles 56 through the contoured tissue for placement of sutures 52C in the purse string configuration. As described for transmural access, the vertical tissue cutting blade 68 is guided through the held tissue to create a tissue incision 101. This incision, which can be cut either fully or partially through the wall of the esophageal tissue, opens the protective mucosal lining and exposes the submucosal tissue containing the tissue healing elements that can promote actual healing at the wound site.

Passage of a guide wire 80 and utilization of the opening for manipulating other instruments (e.g., an endoscope 85) as illustrated in FIGS. 15J-15L are not required for this plication application. Note, however, that instrument 10 without guide wire 80 must still be removed as shown in FIG. 15K prior to closing the prepared wound with the incision 101 circumscribed by the purse string sutures 52C as shown in FIGS. 15M-15R. Rather, after making a successful incision 101 of FIG. 15H, the instrument is removed and the wound closure steps of FIGS. 15M-15R are promptly initiated. To bulk up and tighten the distal esophagus thereby enhancing the effect of the anti-reflux valve naturally located there, the suture 52 is drawn tight to close the wound. A surgical knot or mechanical fastener 91 (FIGS. 15P-15R) is applied to secure the suture 52C, which is trimmed of its redundant suture tails. Further wound site manipulation should be avoided to optimize the potential of successful plication healing.

FIG. 16 is a perspective view of an instrument 12 in accordance with a second preferred embodiment of this invention. This embodiment has the same features and functions as the instrument 10 of the first preferred embodiment of FIG. 1, except its distal tip 44 is shown with a different tissue engaging jaw 44R and it incorporates a horizontal cutting blade instead of a vertical cutting blade.

FIG. 17A is a partial section view of the distal tissue engaging tip 44 of the instrument 12 of FIG. 16 showing a needle 56 in a needle track 44A and ferrule 52A with suture 52C both located in a ferrule pocket 44F abutting against a ferrule stop 44G. The angled horizontal cutting blade 46 is guided by a blade track 44B when it is pulled by blade wires 48. The longer tissue jaw 44R of this embodiment consists of three distal gaps (proximal, middle and distal) 44D and two projecting tissue septums (proximal and distal) 44E to provide for two more tissue engagement bites to form a double pleat in the tissue with both needles in this purse string suture configuration. A vertical perforated wall 44H defines the proximal boundary of tissue jaw 44R. Note arrows indicating views through A-A and through B-B.

FIG. 17B is a section view through A-A of FIG. 17A. This view highlights tissue chamber 44K, which is separated from the upper opening in the tissue jaw 44R by the path of the horizontal blade 46. Vacuum channels 44N communicate through vacuum slots 44L with tissue chamber 44K. The vacuum is also transferred through the vacuum perforations 44M in vertical perforated wall 44H.

FIG. 17C is a section view through B-B of FIG. 17A showing the horizontal cutting blade 46 with its angled sharp edge 46A along with its attached wire pulling members 48 from instrument 12 of FIG. 16. Separated wire blade pulling members 48 can be attached to themselves 48B or to the horizontal blade 46 at location 48A by means such as welding, brazing or gluing. The bottom tissue contact surface 44C of tissue chamber 44K represents the deepest tissue engagement surface. Vacuum openings 44M provide vacuum to the bottom of each tissue gap 44D.

FIGS. 18A, 18B and 18C show the distal tip of the instrument 12. These perspective views illustrate the horizontal blade 46 passage over tissue receiving chamber 44K. FIG. 18A shows the needles 56 exiting the vertical perforated wall 44H and partially advanced into the middle tissue gap 44D. FIG. 18B shows the needles 56 fully advanced into ferrules 52A (not shown) with the horizontal blade 46 partially pulled back towards the vertical perforated wall 44H. FIG. 18C again shows the needles 56 fully advanced, but now the horizontal blade is shown entering under the vertical perforated wall 44H to create a shearing edge.

FIG. 19 is a perspective section view of the left half of the distal tip 44 of instrument 12 of FIG. 16. This partial cut-away illustrates how this instrument engages a lesion 104 attached to the wall of a tubular tissue structure 102 within its tissue receiving chamber 44K in jaw 44R. Note how the lesion 104 is positioned between the horizontal blade 46, the wire blade pulling members 48 and the vertical perforated wall 44H.

FIG. 20A is a partial section view of the distal tip 44 of the instrument 12 inside of a tubular tissue structure 102 containing a lesion 104. Tissue receiving jaw 44R is positioned to receive lesion 104 and its adjacent wall tissue and to form a pleat in the tissue proximate the lesion. FIG. 20B shows the effects of the vacuum causing the distal tip 44 inside of a tubular tissue structure 102 to now draw the lesion 104 into the jaw 44R. The adjacent wall tissue is shown drawn over the tissue gaps 44D and tissue projection septums 44E and into tissue chamber 44K. Needles 56 and ferrules 52A attached to suture 52C remain in their original positions. FIG. 20C appears similar to FIG. 20B, except her e the needles 56 are shown fully advanced through the contoured tissue and into the ferrules 52A.

FIG. 20D represents the next step after FIG. 20C. The needles 56 are now retracted back to their original position along with the ferrules 52A and attached suture 52C to create a purse string configuration. Note the horizontal cutting blade 46 is in its distal starting position. FIG. 20E shows the horizontal cutting blade 46 now in its most proximal position having amputated off the lesion 104 along with surrounding wall tissue, which is now contained within tissue chamber 44K. FIG. 20F shows the distal tip 44 of the instrument 12 of FIG. 16 now released from the inside of a tubular tissue structure 102 with the purse string suture 52C in place through its undulating course within the surrounding tissue.

Recently, at a Harvard/Brigham and Woman's Hospital research facility in Boston, we conducted a series of laboratory studies of this first embodiment of this invention for use in transmural access. The new technology enabled the remote placement of a single suture in a purse string configuration (i.e., a series of bites into and out of the wall in a plane of tissue) around a transmural incision. The abstract form our first ex vivo entitled, "EVALUATING AN OPTIMAL GASTRIC CLOSURE METHOD FOR TRANS-GASTRIC SURGERY," was selected for presentation at the SAGES conference in Dallas on Apr. 29, 2006.

This presentation will compare "the effectiveness of various techniques for gastrotomy closure by assessing leak pressures in an ex vivo porcine stomach model." This abstract includes: "Results: The unclosed controls demonstrated air leakage at a mean pressure of 15 mm Hg (95% Cl: 14-16), representing baseline system resistance. The QuickClip closures leaked air at a mean pressure of 34.2 mm Hg (95% Cl: 20.7-47.6). The prototype gastrotomy device yielded a mean air leak pressures of 98 mm Hg (95% Cl: 23.9-172.0), while dramatically diminishing time for incision and hole closure to approx. 5 minutes. The hand-sewn closures leaked air at a mean pressure of 52.2 mm Hg (95% Cl: 21.2-83.2) . . . Conclusions: The prototype gastrotomy device decreases procedure time and yields leak-resistant gastrotomy closures that are superior to clips and rival hand-sewn interrupted stitches."

Results from the survivor studies from this research were accepted for presentation at the next Digestive Disease Week conference in May 2006. This abstract from the in vivo study, "Transcolonic Access to the Peritoneal Cavity Using a Novel Incision and Closure Device," notes "Closure of transluminal incisions can be performed using a variety of techniques, however these are technically demanding and inconsistent. Here we report the use of a novel combined incision and closure device from LSI Solutions . . . Results. The colonic incision was easily performed and peritoneal cavity accessed without difficulty using the LSI device. Following endoscope withdrawal into the lumen, complete closure was achieved in under one minute using the device. All animals survived 14 days without apparent sequelae before elective sacrifice. At necropsy, limited pelvic adhesions were identified and the incision sites were completely closed and well healed. Conclusion. Use of this novel incision and closure device allows transcolonic access to the peritoneal cavity in addition to the rapid, complete, and reproducible closure of the colonic incision. This will likely improve the efficiency and safety of translumenal procedures."

While the invention has been described in connection with a number of presently preferred embodiments thereof, those skilled in the art will recognize that many modifications and changes may be made therein without departing from the true spirit and scope of the invention which accordingly is intended to be defined solely by the appended claims.

The invention claimed is:

1. A tissue suturing instrument comprising:
    a handle having a single operating control on the handle;
    an elongated body extending from the handle to a distal end;
    a tip at a distal end of the elongated body;
    a tissue receiving region in the tip;
    at least one projection disposed along a first side of the tissue receiving region dividing the side of the tissue receiving region into first and second portions for lifting a tissue section away from a base of the tissue receiving region while leaving a substantially continuous center region;
    first and second retractable needles coupled to the operating control and selectively simultaneously extending across the first and second portions of the tissue receiving region adjacent the at least one projection and through a lifted tissue section and simultaneously retracting there through; and
    a suture having first and second ends disposed at a distal end of the tissue receiving region, the first and second ends engaging the first and second retractable needles when the needles are extended across the tissue receiving region, and being simultaneously carried proximally across the regions by the needles when the needles are retracted.

2. The tissue suturing instrument of claim 1 in which the tissue receiving region comprises:
    a tissue receiving surface;
    a suction source; and
    at least one passage coupling the suction source to the surface and attracting tissue to the surface.

3. The tissue suturing instrument of claim 2 comprising a suction fitting on a proximal end of the elongated body communicating with the at least one passage.

4. The tissue suturing instrument of claim 1 in which the tissue receiving region is defined by two sides and two ends, the sides being longer than the ends.

5. The tissue suturing instrument of claim 4 comprising a second projection disposed along another of the sides.

6. The tissue suturing instrument of claim 5 comprising two projections, one disposed along each of the two sides.

7. The tissue suturing instrument of claim 6 in which the two projections are rounded.

8. A tissue suturing instrument as set forth in claim 1 further comprising:
a movable cutter disposed in the tissue receiving region.

9. A tissue suturing instrument as set forth in claim 8 in which the cutter is arranged generally perpendicular to the tissue receiving region.

10. A tissue suturing instrument as set forth in claim 8 in which the cutter is arranged generally parallel to the tissue receiving region.

11. A tissue suturing instrument as set forth in claim 8 in which the tissue receiving surface comprises a slot and the cutter comprises a follower riding in the slot.

12. The tissue suturing instrument as set forth in claim 8 in which the cutter comprises a blade attached to a cutter shuttle.

13. The tissue suturing instrument of claim 12 in which the blade comprises a sharpened proximal surface.

14. The tissue suturing instrument of claim 13 in which the blade comprises a sharpened tip.

15. The tissue suturing instrument of claim 8 comprising a second control on the handle, linked to the cutter operative to move the cutter distally and proximately in response to operator input from the handle.

16. The tissue suturing instrument of claim 15 in which the second control comprises a longitudinally reciprocating actuator.

17. The tissue suturing instrument of claim 16 in which the longitudinally reciprocating actuator comprises a hollow tube.

18. The tissue suturing instrument of claim 8 in which the tissue receiving region comprises a longitudinal slot, and the movable cutter moves in the slot.

19. The tissue suturing instrument of claim 18 in which the tissue receiving region comprises
first and second tissue receiving surfaces on opposite sides of the slot;
a suction source; and
at least one passage coupling the suction source to each of the first and second tissue receiving surfaces and attracting tissue to the surfaces.

20. The tissue suturing instrument of claim 19 comprising first and second passages coupling the suction source to the first and second tissue receiving surfaces respectively.

21. The tissue suturing instrument of claim 8 in which the movable cutter comprises a channel for passing a guide wire.

22. The tissue suturing instrument of claim 1 comprising a channel extending through the elongated body from the distal end to the handle and in which the suture is partially disposed in the channel.

23. The tissue suturing instrument of claim 22 comprising a chamber in the handle having a transparent window, the chamber containing a portion of the suture.

24. The tissue suturing instrument of claim 1 in which the elongated body comprises a flexible body.

25. A tissue suturing instrument comprising:
a handle having an operating lever on the handle;
an elongated body extending from the handle to a distal end;
a tip at a distal end of the elongated body;
a tissue receiving region in the tip;
at least one projection dividing the tissue receiving region into first and second portions;
first and second retractable needles coupled to the operating lever and selectively extending across the first and second portions of the tissue receiving region and retracting there through;
a movable cutter disposed in the tissue receiving region
a control on the handle having a longitudinally reciprocating actuator and a hollow tube;
the control linked to the cutter operative to move the cutter distally and proximately in response to operator input from the handle and in which the actuator comprises a knob on the proximal end thereof having an opening for receiving a guide wire; and
a suture having first and second ends disposed at the distal end of the tissue receiving region, the first and second ends engaging the first and second retractable needles when the needles are extended across the tissue receiving region, and being simultaneously carried proximally across the regions by the needles when the needles are retracted.

26. The tissue suturing instrument of claim 25 in which the knob comprises a seal for ceiling to the guide wire.

27. A tissue suturing instrument comprising:
a handle having an operating lever on the handle;
an elongated body extending from the handle to a distal end;
a tip at a distal end of the elongated body;
a tissue receiving region in the tip;
at least one projection dividing the tissue receiving region into first and second portions;
first and second retractable needles coupled to the operating lever and selectively extending across the first and second portions of the tissue receiving region and retracting there through;
a movable cutter disposed in the tissue receiving region; the cutter including a channel for passing a guide wire, the channel having an upturned end portion located distally of the cutter for directing a guide wire away from the tissue receiving region; and
a suture having first and second ends disposed at the distal end of the tissue receiving region, the first and second ends engaging the first and second retractable needles when the needles are extended across the tissue receiving region, and being simultaneously carried proximally across the regions by the needles when the needles are retracted.

* * * * *